(12) United States Patent
Mochizuki

(10) Patent No.: US 8,454,521 B2
(45) Date of Patent: Jun. 4, 2013

(54) SPHYGMOMANOMETER

(75) Inventor: Hiroshi Mochizuki, Kawaguchi (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 11/662,207

(22) PCT Filed: Sep. 12, 2005

(86) PCT No.: PCT/JP2005/016768
§ 371 (c)(1),
(2), (4) Date: Mar. 18, 2008

(87) PCT Pub. No.: WO2006/028248
PCT Pub. Date: Mar. 16, 2006

(65) Prior Publication Data
US 2008/0312544 A1      Dec. 18, 2008

(30) Foreign Application Priority Data

Sep. 10, 2004   (JP) ................................. 2004-264562

(51) Int. Cl.
*A61B 5/02* (2006.01)

(52) U.S. Cl.
USPC ............ 600/485; 600/481; 600/492; 600/494

(58) Field of Classification Search
USPC .................. 600/492, 490, 488, 485; 128/900
See application file for complete search history.

(56) References Cited

U.S. PATENT DOCUMENTS

| | | | | |
|---|---|---|---|---|
| 3,779,236 A | * | 12/1973 | Stewart | 600/498 |
| 4,475,557 A | * | 10/1984 | Hatschek et al. | 600/494 |
| 4,552,153 A | | 11/1985 | Newman et al. | |
| 5,022,403 A | * | 6/1991 | LaViola | 600/493 |
| 5,285,791 A | * | 2/1994 | Smith | 600/490 |
| 5,551,438 A | * | 9/1996 | Moses | 600/485 |

(Continued)

FOREIGN PATENT DOCUMENTS

| AU | 669172 B2 | 1/1994 |
|---|---|---|
| EP | 1 310 210 A | 5/2003 |

(Continued)

OTHER PUBLICATIONS

English translation of Form PCT/ISA/237 (Written Opinion of the International Searching Authority).

(Continued)

*Primary Examiner* — Patricia Mallari
*Assistant Examiner* — Michael D'Angelo
(74) *Attorney, Agent, or Firm* — Buchanan Ingersoll & Rooney PC

(57) ABSTRACT

The objective of the present invention is to provide a sphygmomanometer that is easy to use. The sphygmomanometer according to the present invention measures blood pressure in accordance with an oscillation in an artery wall, resulting from an arterial pulse correspondent with a change in cuff pressure. It comprises a cuff that is connected to the sphygmomanometer main body by a tube, a display unit for displaying the results of blood pressure measurements, and an air supply unit for supplying air to, and thus pressurizing, the cuff, which is detachable from the sphygmomanometer main body. The air supply unit is screwed into the sphygmomanometer main body with a screw assembly, and the screwed-in state is preserved by a caulking ring. The air supply unit also comprises a filter for keeping dust from entering the sphygmomanometer main body.

4 Claims, 27 Drawing Sheets

U.S. PATENT DOCUMENTS

| | | | | |
|---|---|---|---|---|
| 6,315,734 | B1 * | 11/2001 | Nunome | 600/500 |
| 6,322,517 | B1 * | 11/2001 | Yamamoto et al. | 600/494 |
| 2002/0170359 | A1 * | 11/2002 | Yamakoshi et al. | 73/756 |
| 2004/0181254 | A1 | 9/2004 | Choi et al. | |

FOREIGN PATENT DOCUMENTS

| | | | |
|---|---|---|---|
| EP | 1310210 A2 * | 5/2003 | |
| GB | 920970 A | 3/1963 | |
| GB | 1 511 076 A | 5/1978 | |
| GB | 2 153 535 A | 8/1985 | |
| GB | 2153535 A * | 8/1985 | |
| JP | 56-152625 A | 11/1981 | |
| JP | 61-79440 A | 4/1986 | |
| JP | 61-90638 A | 5/1986 | |
| JP | 6-70893 A | 3/1994 | |
| JP | 6-154174 A | 6/1994 | |
| JP | 2000-161577 A | 6/2000 | |
| JP | 2004-81743 A | 3/2004 | |

OTHER PUBLICATIONS

European Search Report dated Jan. 18, 2008.

Accuracy and applicability of the Terumo ES-H55 double-cuff sphygmomanometer for hospital use; Osamu Tochikubo, Kiyoko Nishijima, Kenji Ohshige and Kazuo KimuraDevices and Technology, vol. 8, No. 5, 2003; pp. 203-209.

A New Double Cuff Sphygmotonometer for Accurate Blood Pressure Measurement; Osamu Tochikubo, Junko Watanabe, Kouichi Hanada, Eiji Miyajima and Kazuo Kimura, Hypertens.Res., vol. 24, No. 4, 2001.

* cited by examiner

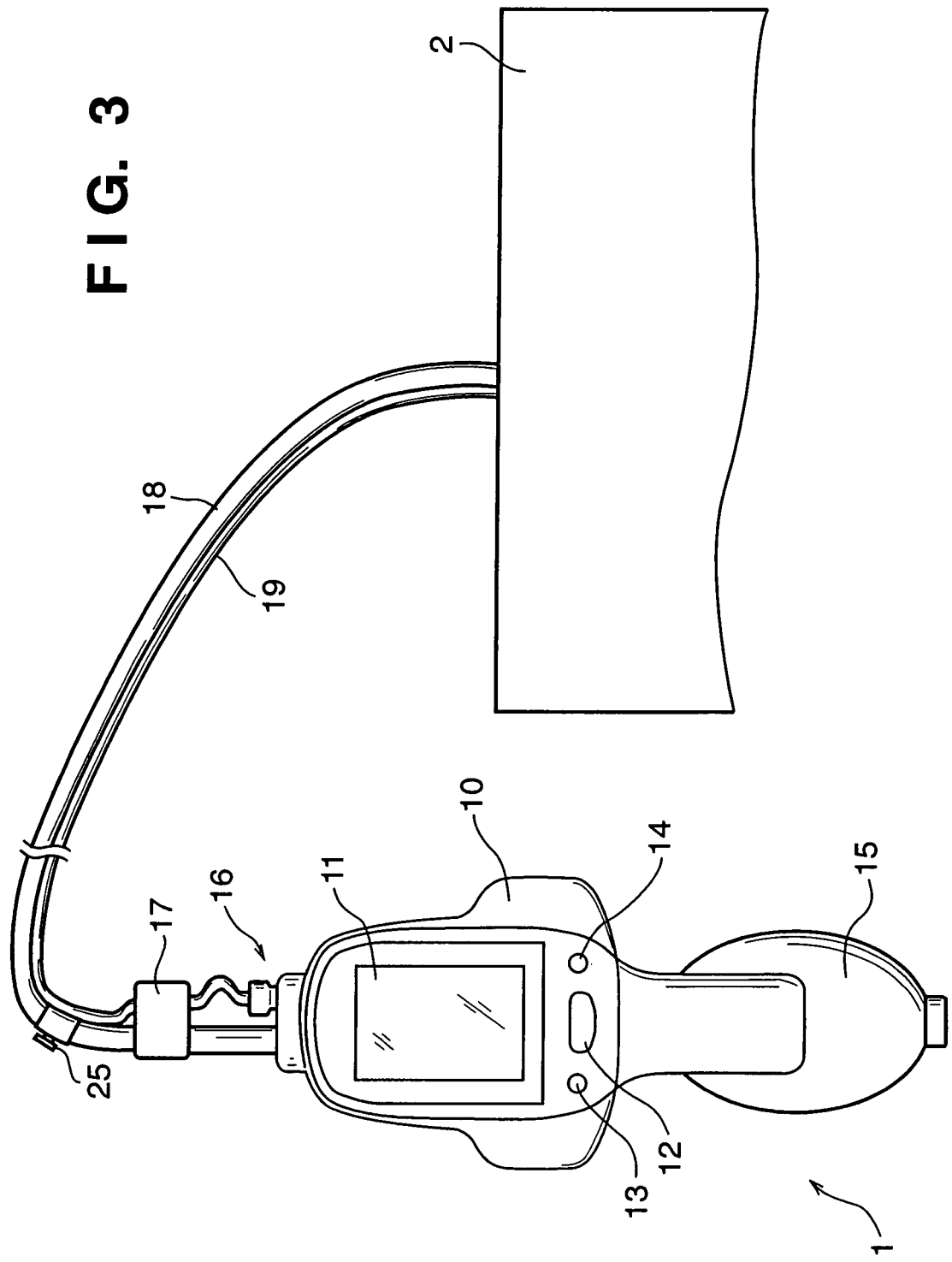

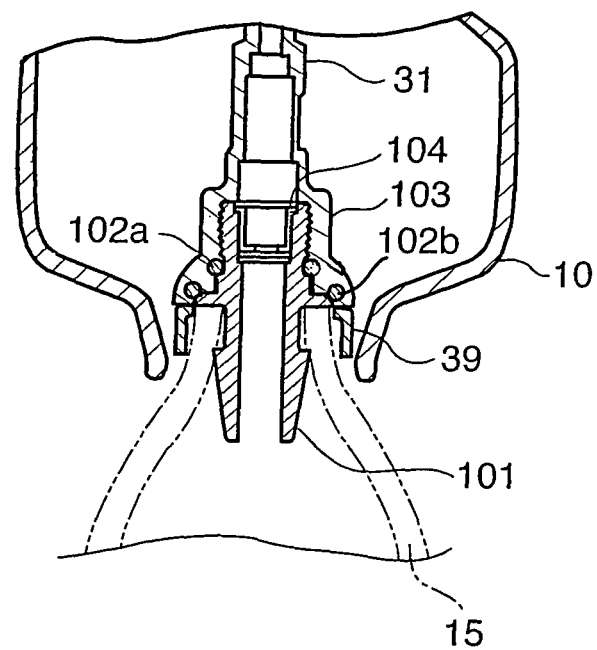
F I G. 10A

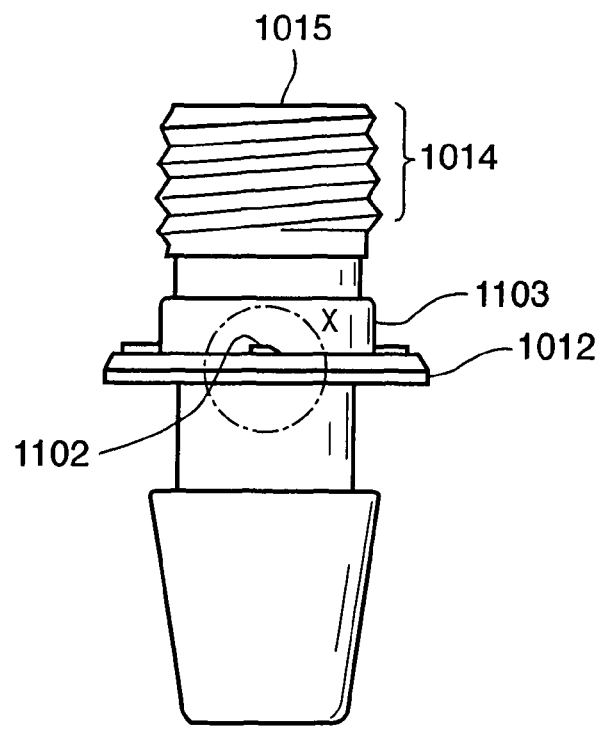
F I G. 11A
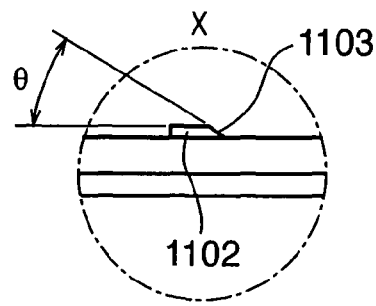
F I G. 11B
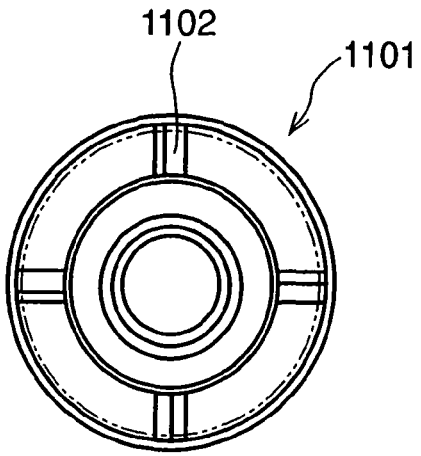
F I G. 11C

CHANNEL

F I G. 20
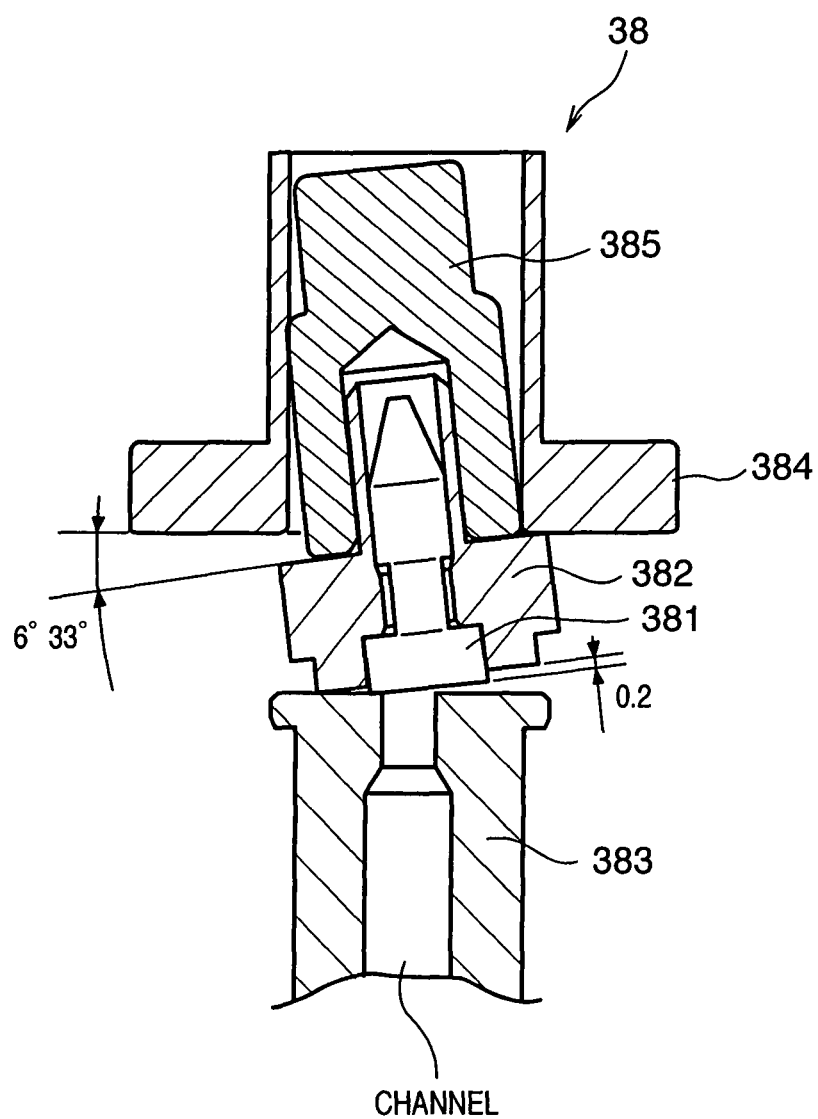

SPHYGMOMANOMETER

FIELD OF THE INVENTION

The invention relates to a sphygmomanometer that is used in a hospital or other facility, by a nurse or other medical professional, to measure a patient's blood pressure, and, in particular, that is portable and allows selecting from a plurality of types of cuffs.

DESCRIPTION OF THE RELATED ART

A sphygmomanometer that sends air from an air supply sphere, i.e., a rubber bulb, to a cuff, via the sphygmomanometer main body, is disclosed in, for example, the cited reference 1 and 2.

FIG. 1 depicts a sphygmomanometer comprising a Korotkov sound sensor as disclosed in the cited reference 1. In the sphygmomanometer depicted in FIG. 1, a sphygmomanometer main body 1301 and a cuff 1302 are joined by a rubber tube 1304 and a lead line 1305. A rubber bulb that supplies air 1303 is also connected to the cuff 1302.

FIG. 2 depicts a sphygmomanometer as disclosed in the cited reference 2. The sphygmomanometer comprises a flexible first air tube 1405 and a second air tube 1406 that communicate with either a sphygmomanometer main body 1401 and a cuff 1404, or the sphygmomanometer 1401 and the open atmosphere, with the tubes less likely to interfere with a display unit 1402 or a control unit 1403, owing to the relation between the first air tube 1405 and the second air tube 1406 being configured as depicted in FIG. 2, thus making the display easier to see, and the power switch and other aspects of the control unit 1403 easier to operate.

Cited Reference 1: Japanese Patent Publication Laid Open 61-79440
Cited Reference 2: Japanese Patent Publication Laid Open 2004-81743

DISCLOSURE OF INVENTION

Problems to Be Solved by the Invention

The sphygmomanometers disclosed in the cited reference 1 and 2, however, have the air supply sphere connected, via the air tube, either to the cuff or to the sphygmomanometer main body, and thus, the sphygmomanometer main body must be maintained with one hand, and the air supply sphere held, and pressure applied, with the other hand, resulting in poor usability.

Another problem is that connecting the respective units by tubes, as per the sphygmomanometers disclosed in the cited references 1 and 2, increases the overall size of the sphygmomanometer.

The present invention, devised with the foregoing problems in mind, has as its objective the provision of a smaller, portable, easy to use sphygmomanometer.

Means for Solving the Problems

In order to achieve the objective, the sphygmomanometer according to the present invention measures blood pressure based on a fluctuation in an artery wall resulting from an arterial pulse in accordance with a change in cuff pressure. It comprises a cuff that is connected to a sphygmomanometer main body by a tube, a display unit for displaying results of measuring blood pressure, and an air supply sphere for delivering air to, and pressurizing, the cuff, wherein the air supply sphere is detachable from the sphygmomanometer main body, constituting a portion of the sphygmomanometer main body when attached to the sphygmomanometer main body.

The air supply sphere comprises a connector unit for connecting the air supply sphere to the sphygmomanometer main body, and a filter within the connector unit for preventing dust from entering the sphygmomanometer main body.

The connector unit is screwed into the sphygmomanometer main body by a screwing assembly, and is maintained in the screwed-in state by a ring of caulk.

A sphygmomanometer disclosed in claim 2, wherein an o-ring is fitted into the screwing assembly of the air supply sphere, such that the air supply sphere will be disengaged from the sphygmomanometer main body only with difficulty.

An o-ring is fitted into the screwing assembly of the air supply sphere, such that the air supply sphere will be disengaged from the sphygmomanometer main body only with difficulty.

It is permissible to fit a ring, other than an o-ring, that possesses a one-way clutch assembly, to the air supply sphere's screwing assembly, and a protrusion is formed wherein the one-way clutch assembly fits.

The cuff is selected from among a plurality of types of cuffs of different sizes.

The cuff comprises a large cuff, to stop blood flow, and a small cuff, for detecting a pulse. A unit of the large cuff that connects the large cuff to the tube is made with a protrusion that has a tapering portion. A unit of the small cuff that connects the small cuff to the tube is made to connect to the small cuff by being slackened and twisted vis-à-vis the large cuff tube, the outer diameter of which is larger than that of the small cuff tube.

Other characteristics of the present invention will be apparent from the disclosures of the preferred embodiments and the attached drawings, as given hereinafter.

Effect of the Invention

According to the sphygmomanometer of the previous invention, the tube for connecting the air supply sphere to the sphygmomanometer main body is eliminated, making the two components into a single unit, allowing one-handed air supply and pressurization, tremendously improving ease of use, and allowing miniaturization of the overall size of the sphygmomanometer.

Other characteristics and advantages of the present invention will be apparent from the following descriptions, with reference to the attached drawings. Portions of the attached drawings that are identical or substantially similar to one another will be designated with identical reference numbers.

BRIEF DESCRIPTION OF DRAWINGS

The attached drawings are included with the specification and constitute a portion thereof. They are used to depict the embodiment of the invention, and to describe the principles of the invention, together with the descriptions thereof.

FIG. 3 depicts an external view of a sphygmomanometer according to the embodiment.

FIGS. 10A, 10B, and 10C depict an assembly of a connection unit between an air supply sphere 15 and the sphygmomanometer main body.

FIGS. 11A, 11B, and 11C depict an assembly of a connection unit between an air supply sphere 15 and the sphygmomanometer main body 10, according to a different concrete example of a connector.

FIG. 20 depicts a circumstance wherein a tilt has occurred within a rubber valve 381 of the electromagnetic valve 38.

BEST MODE FOR CARRYING OUT THE INVENTION

Figure 1:
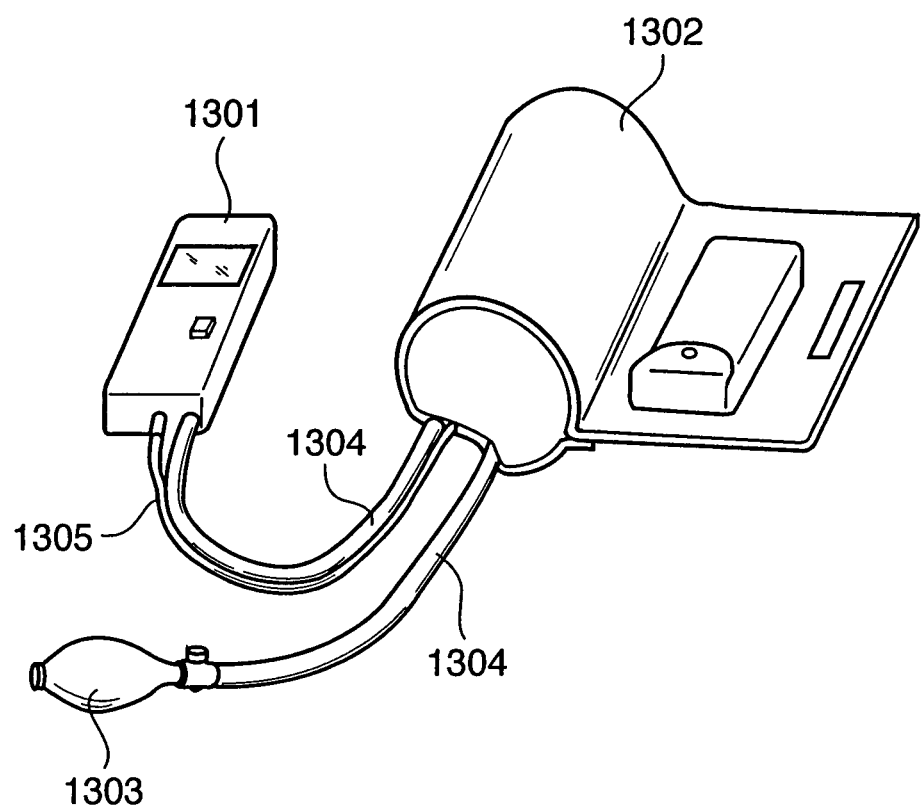
FIG. 1 depicts a first concrete example of a conventional sphygmomanometer.
Figure 2:
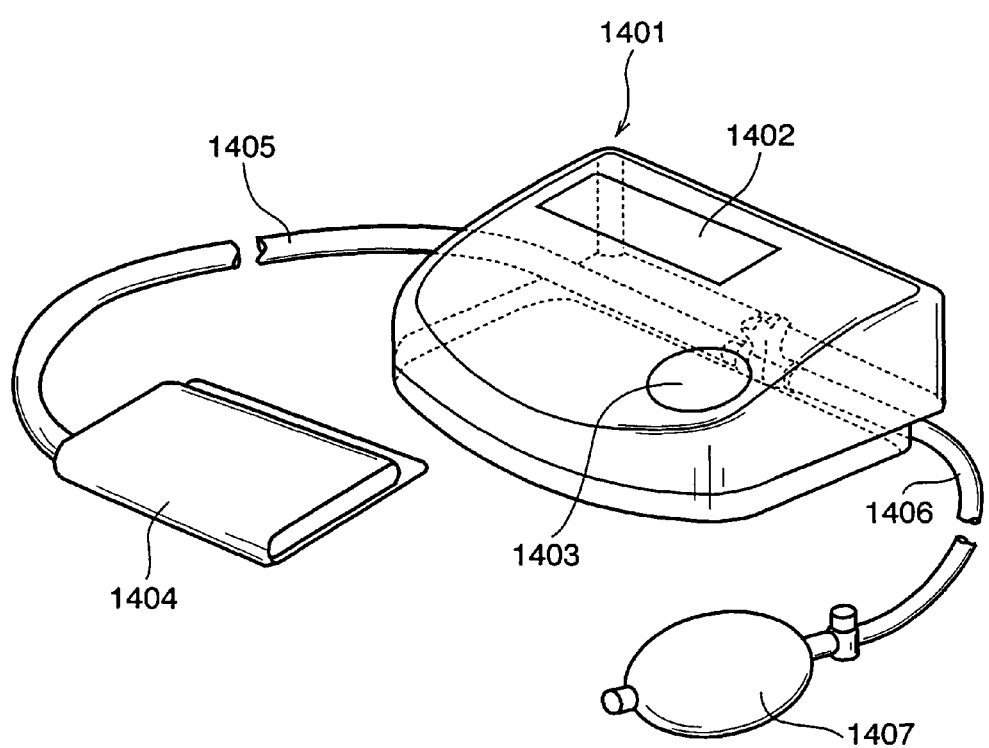
FIG. 2 depicts a second concrete example of a conventional sphygmomanometer.

Following is a detailed description of the embodiments of the invention, with reference to the attached drawings.

<Sphygmomanometer External View>

FIG. 3 depicts an external view of a sphygmomanometer 1 and a cuff 2 according to the embodiment.

In FIG. 3, No. 10 is a casing of a sphygmomanometer main body, within which are contained a substrate, upon which is carried an electrical circuit for electrically operating the sphygmomanometer 1, and a tube, described hereinafter, for sending air to, and exhausting air from, a cuff 2, the latter of which in turn comprises a large cuff 22, that is, a large-capacity air bag, and a small cuff 23, that is, a small-capacity air bag, which are both described hereinafter. No. 11 is a display unit, wherein are displayed such elements as a systolic and a diastolic blood pressure value, a pulse rate, and a measurement mode. No. 12 is an On/Off Power Switch, and No. 13 is a mode switch. Regarding a mode of the sphygmomanometer 1 according to the embodiment, which will be described hereinafter, there are a plurality of measurement modes, three in the present instance, that are built into the sphygmomanometer 1, being a normal mode, a slow mode, and a stethoscope mode. No. 14 is an exhaust switch, and pressing thereupon allows air in the large cuff 22 to be forcibly exhausted. No. 15 is an air supply sphere, i.e., a rubber bulb, which supplies air to the cuff 2 via the tube within the casing 10 by repeated squeezing and releasing.

The air from the air supply sphere 15 is sent to the cuff 2 via a tube 18 and a tube 19 that are connected to a connector unit 16. No. 18 is a tube for sending air to the large cuff 22, i.e., a large cuff tube, and No. 19 is a tube for sending air to the small cuff 23, i.e., a small cuff tube.

No. 17 is a tube holder, for preventing the large cuff tube 18 and the small cuff tube 19, which are a single unit from the point of the tube holder 17 on toward the cuff 2, from separating from one another. By making the small cuff tube 19 flexible, i.e., keeping it from being strained, between the connector unit 16 and the tube holder 17 makes it difficult for the small cuff tube 19 from being disconnected from the connector unit 16. It is possible to avoid the small cuff tube 19 coming apart from the connector unit 16, even if the tube is tugged on, or if the tube is pulled in a direction that it most likely was not meant to go, such that the large cuff tube 18 will not come loose, to the extent that strain is kept off the small cuff tube 19.

The cuff 2 is covered with a cuff cover 21, within which is the large-cuff 22, which is formed of a flexible material, which may include, but is not limited to, natural rubber, synthetic rubber, or an elastomer, and the small cuff 23, which is formed of a flexible material, which may include, but is not limited to, polyurethane.

<Composition of the Cuff>

Figure 4A:
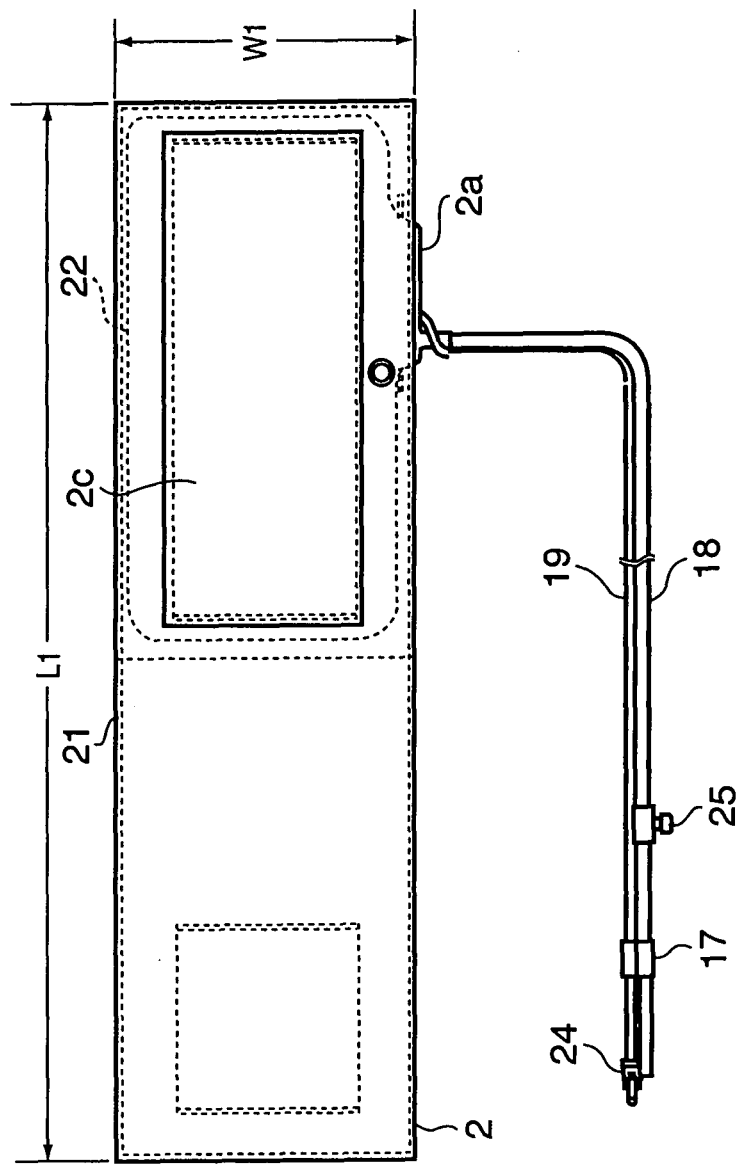
FIG. 4A and FIG. 4B depict an assembly of a cuff 2 according to the embodiment.
Figure 4B:
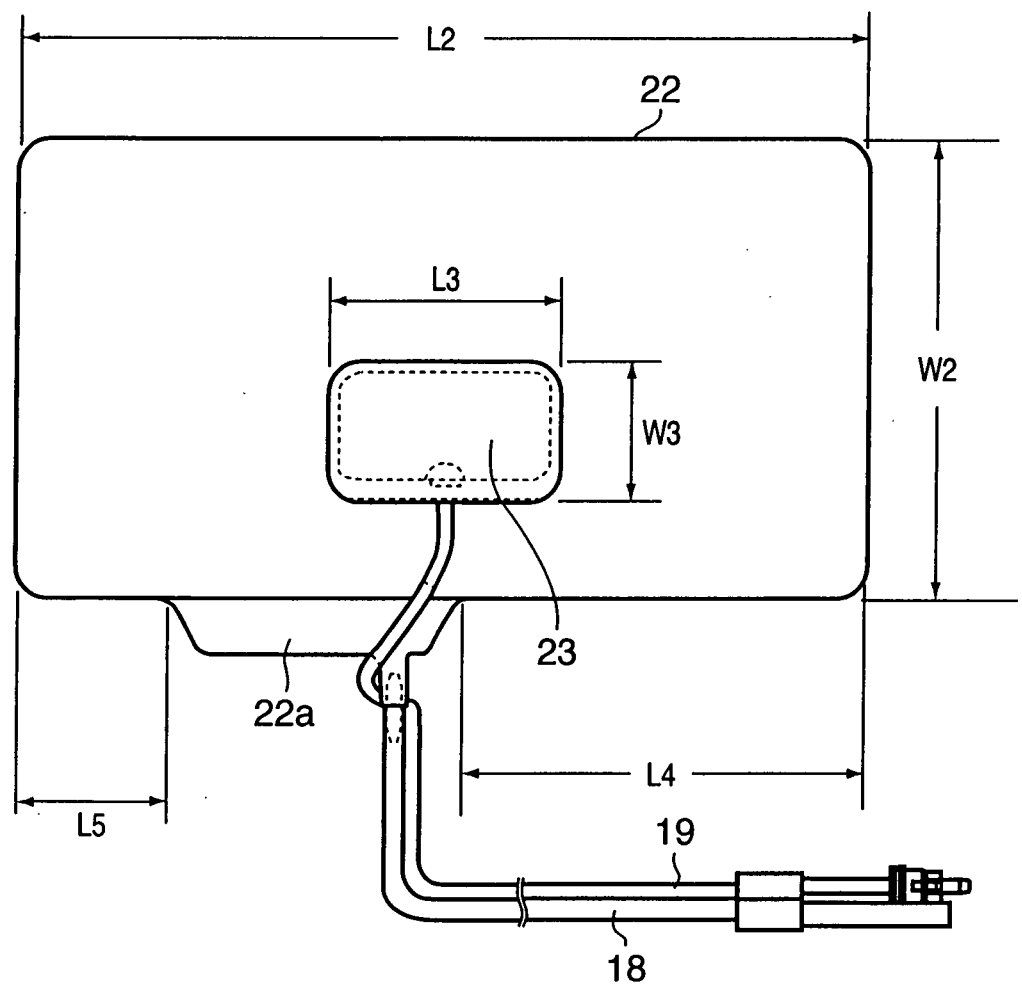

FIG. 4A and FIG. 4B depict an assembly of the cuff 2. FIG. 4A depicts whole structure, and FIG. 4B depicts a structure of the large cuff 22 and the small cuff 23. As depicted in FIG. 4A, the cuff 2 comprises the cuff cover 21, in which is a surface fastener on an outer surface (not shown), and the large cuff 22 and the small cuff 23, which are covered by the cuff cover 21. It is possible to, for example, replace or disinfect the cuff 2, and a protrusion portion 22a, with a taper unit 22b, is made a part of the large cuff 22, in order that the large cuff 22 and the small cuff 23 may be easily inserted into, and removed from, an opening 2a. When the protrusion portion 22a is inserted into the cuff 2, the protrusion portion 22a corresponds to the position of the opening 2a. The protrusion portion 22a is placed in a position off-center in the lengthwise direction of the cuff 22, i.e., L4 is greater than L5, to avoid being inserted backwards.

The large cuff 22 is pressurized by air supplied thereto via the large cuff tube 18. By being pressurized and inflated, the large cuff 22 cuts off blood flow to an arm, around which the cuff 2 is wrapped, of a person whose blood pressure is being measured. The small cuff 23 is also pressurized by air supplied thereto, via the small cuff tube 19. When air pressure in the large cuff 22 is reduced by exhaust, and blood flow is restored, a fluctuation occurs in the pressure of the air in the small cuff 23, and a pulse wave that corresponds to the fluctuation is detected by a pressure sensor 92 (see FIG. 14 for details). A backing sheet made of PET (not shown) is placed between the large cuff 22 and the small cuff 23, which is engineered so as to facilitate detection of a slight pressure fluctuation within the small cuff 23. Given that the large cuff 22 possesses elasticity in its inflated state, placing the small cuff 23 directly next to the large cuff 22 would have a potential for failing to detect the pressure fluctuation within the small cuff 23, even if the fluctuation should be present. To avoid such a circumstance, the small cuff tube 19 is slackened and twisted vis-à-vis the large cuff tube 18, which has an outer diameter that is wider than that of the small cuff tube 19, as the small cuff tube 19 is connected to the small cuff 23. The small cuff tube 19 is twisted once according to the embodiment, although a plurality of twisting is permissible. The assembly has the effect of avoiding the small cuff tube 19 separating when being inserted into, and detached from, the cuff 2. Absorption by slackening and twisting has the effect of avoiding the small cuff tube 19 being snagged when being inserted into, and detached from, the cuff 2.

It is also possible for a nurse to use the surface fastener to securely attach the cuff 2 to an upper arm of a patient, i.e., an examinee. It is not necessary to detach a ring (not shown) to do so. The surface fastener is built in because it becomes more difficult to wrap and secure the cuff 2 as it gets larger.

No. 24 is a tube connector which is connected to the connector unit 16 on the sphygmomanometer main body. No. 25 is a forcible exhaust valve which is built in with a large cuff size, i.e., L or XL. Cuff size will be described hereinafter. With a large cuff size, the large cuff 22 becomes larger out of necessity, and time is required to deflate from a sufficiently inflated state, and it is possible to discharge the air of the large cuff 22 in a short amount of time by opening the forcible exhaust valve 25, when one wants to let the air out of the large cuff 22 rapidly.

A plurality of sizes of cuffs are provided according to the embodiment. In increasing order of size, the sizes are XS, S, M, L, and XL.

With regard to the XS size cuff, for example, a length L1 and a width W1 of the cuff cover 21 is 345 mm plus or minus 5 mm and 100 mm plus or minus 4 mm, a length L2 and a width W2 of the large cuff 22 is 130 mm plus or minus 10 mm and 80 mm plus or minus 5 mm, and a length L3 and a width W3 of the small cuff 23 is 30 mm plus or minus 1 mm and 20 mm plus or minus 1 mm.

With regard to the S size cuff, for example, a length L1 and a width W1 of the cuff cover 21 is 435 mm plus or minus 5 mm and 130 mm plus or minus 4 mm, a length L2 and a width W2 of the large cuff 22 is 170 mm plus or minus 10 mm and 110 mm plus or minus 5 mm, and a length L3 and a width W3 of the small cuff 23 is 40 mm plus or minus 1 mm and 25 mm plus or minus 1 mm.

With regard to the M size cuff, for example, a length L1 and a width W1 of the cuff cover 21 is 520 mm plus or minus 5 mm and 150 mm plus or minus 4 mm, a length L2 and a width W2 of the large cuff 22 is 240 mm plus or minus 10 mm and 130 mm plus or minus 5 mm, and a length L3 and a width W3 of the small cuff 23 is 60 mm plus or minus 1 mm and 30 mm plus or minus 1 mm.

With regard to the L size cuff, for example, a length L1 and a width W1 of the cuff cover 21 is 640 mm plus or minus 5 mm and 190 mm plus or minus 4 mm, a length L2 and a width W2 of the large cuff 22 is 320 mm plus or minus 10 mm and 170 mm plus or minus 5 mm, and a length L3 and a width W3 of the small cuff 23 is 80 mm plus or minus 1 mm and 40 mm plus or minus 1 mm.

With regard to the XL size cuff, for example, a length L1 and a width W1 of the cuff cover 21 is 220 mm plus or minus 4 mm and 830 mm plus or minus 5 mm, a length L2 and a width W2 of the large cuff 22 is 420 mm plus or minus 10 mm and 200 mm plus or minus 5 mm, and a length L3 and a width W3 of the small cuff 23 is 100 mm plus or minus 1 mm and 50 mm plus or minus 1 mm.

<Internal Assembly of a Sphygmomanometer Main Body>

Figure 5:
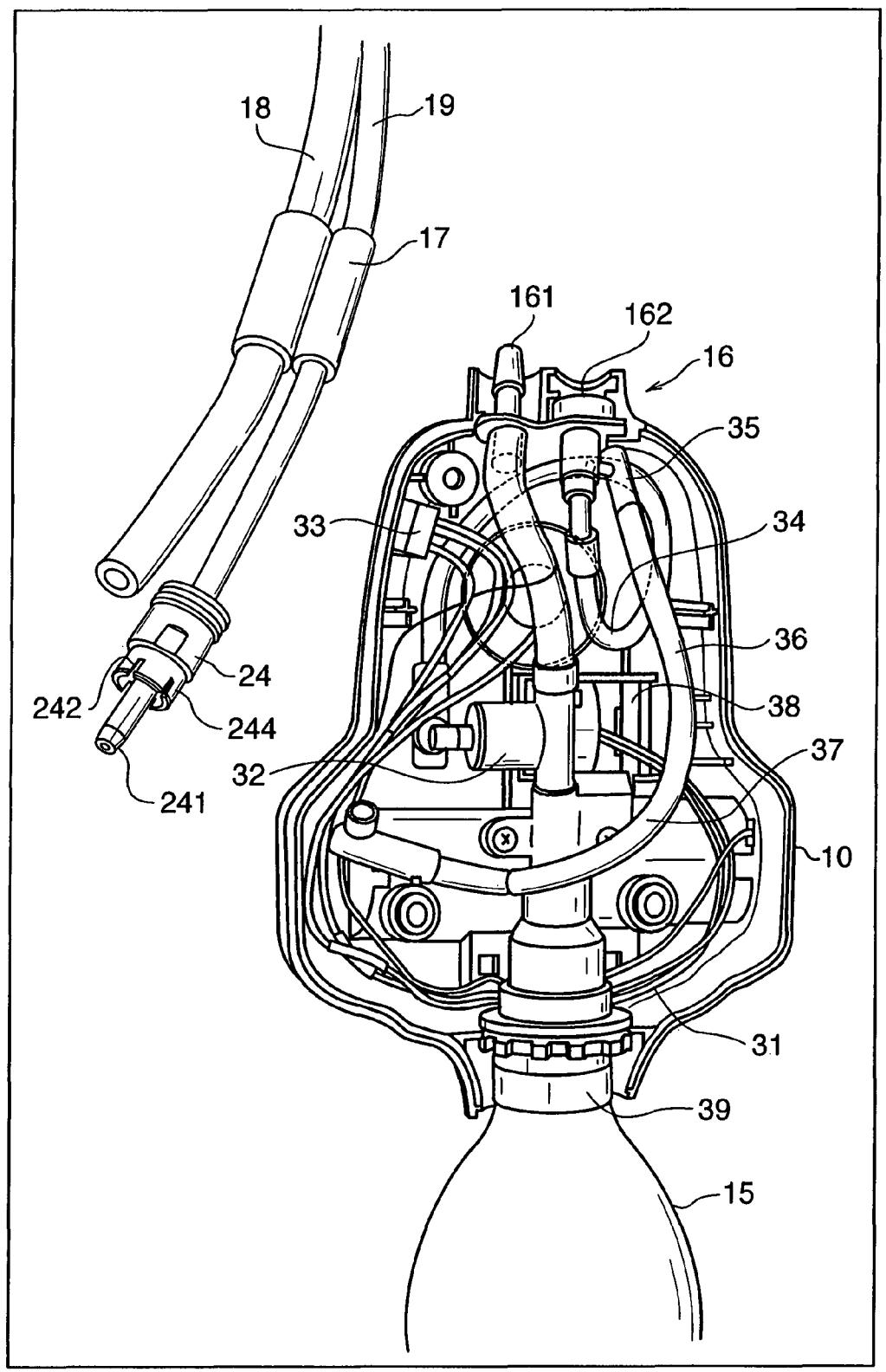
FIG. 5 depicts an internal assembly of a sphygmomanometer main body according to the embodiment.

FIG. 5 depicts an internal assembly of a sphygmomanometer main body 10.

In FIG. 5, No. 31 is a manifold, No. 32 is a manifold junction unit, No. 33 is a large cuff conduit, No. 34 is a bypass tube, i.e., a small cuff conduit, No. 35 is a conduit junction unit, No. 36 is a pressure sensor conduit, No. 37 is a bend prevention coil, No. 38 is an electromagnetic valve, and No. 39 is a caulking ring. No. 161 is a large cuff male connector for connecting the large cuff conduit 33 to the large cuff tube 18, and No. 162 is a small cuff female connector for connecting the small cuff conduit 34 to the small cuff tube 19. The large cuff male connector 161 and the small cuff female connector 162 are formed as a single unit, and form the connector unit 16.

Air supplied from the air supply sphere 15 passes through the manifold 31 and is discharged from the large cuff male connector 161, via the large cuff conduit 33. Air discharged from the large cuff male connector 161 is sent to the large cuff 22, passing through the large cuff tube 18. Thus is the large cuff 22 pressurized.

A portion of the air supplied from the air supply sphere 15 enters the bypass tube 34 from the manifold junction unit 32, and, passing through the bypass tube 34, is discharged from the small cuff female connector 162. Air discharged from the small cuff female connector 162 is sent to the small cuff 23, passing through the small cuff tube 19. Thus is the small cuff 23 pressurized.

Figure 14:
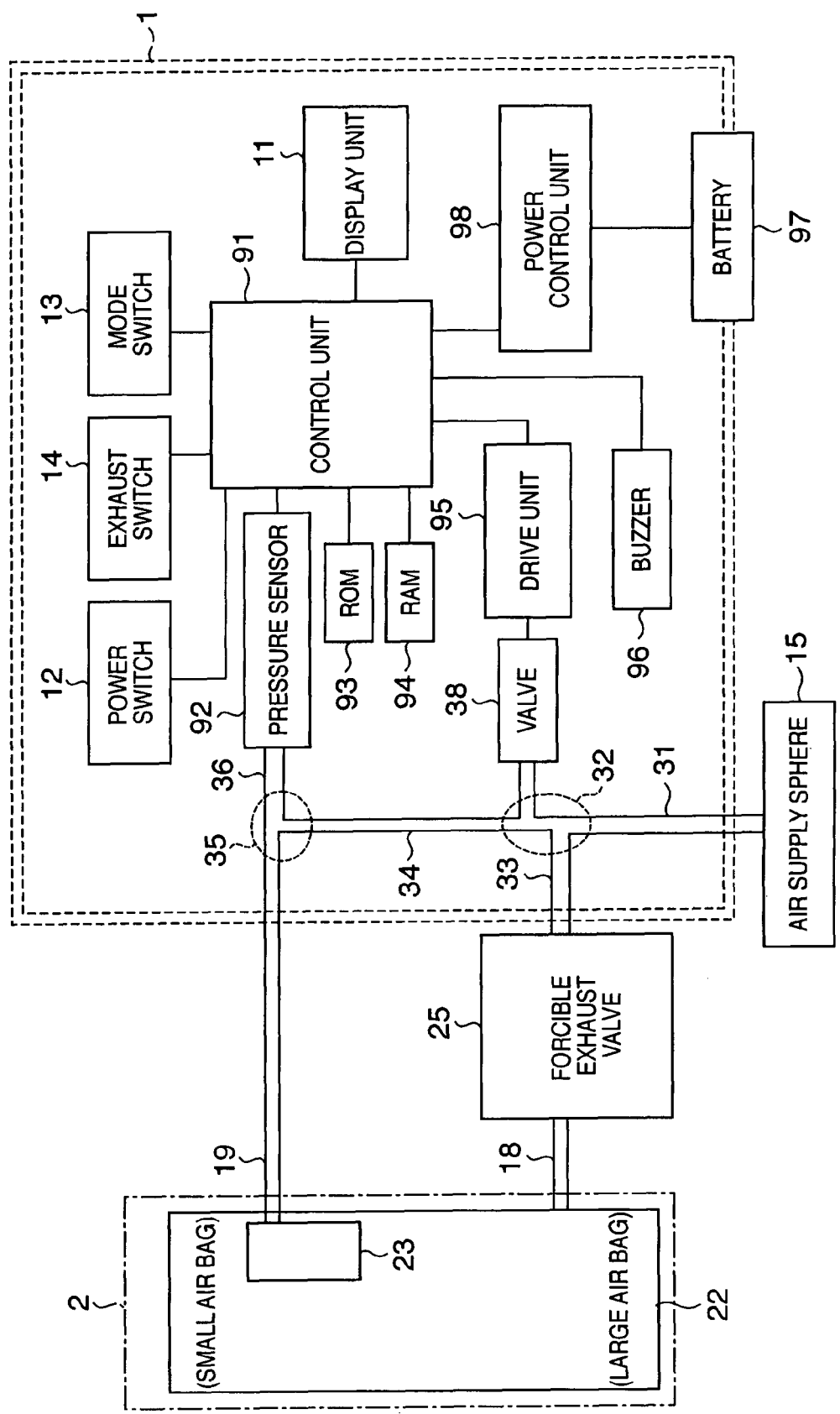
FIG. 14 depicts a circuit block diagram of a sphygmomanometer main body.

The pressure sensor conduit 36, which branches off from the conduit junction unit 35, is in place to both send the portion of air that is routed from the bypass tube 34 to a pressure sensor, i.e., No. 92 in the block diagram in FIG. 14, and also to send the air that is forced out by the pressure of the small cuff 23 that fluctuates with the pressure wave during measurement to the pressure sensor. The bend prevention coil, i.e., a bend prevention unit material, 37 is within the pressure sensor conduit 36, which possesses a function of avoiding the tube being blocked by a breakage of the pressure sensor conduit 36 when the pressure sensor conduit 36 is bent.

The bypass tube 34 is made, for example, from an olefin type of elastomer, has an internal diameter on the order of 0.4 mm, with a narrow-gauge pipe similarly 0.4 mm in diameter, with stainless steel or other metallic property at either end, reinforcing the connectors at either end such that they do not collapse, allowing maintenance of the inner diameter. The electromagnetic valve 38 is controlled to close while air is being sent via the air supply sphere 15, causing sufficient air to be sent to the cuff 2, and to open when exhausting air from, and depressurizing, the large cuff 22. While air is also exhausted from the small cuff 23, the quantity is very small compared with that of the large cuff 22. The open and close control and other aspects of the electromagnetic valve 38 are described hereinafter.

<Connector Unit 16 Assembly>

Figure 6:
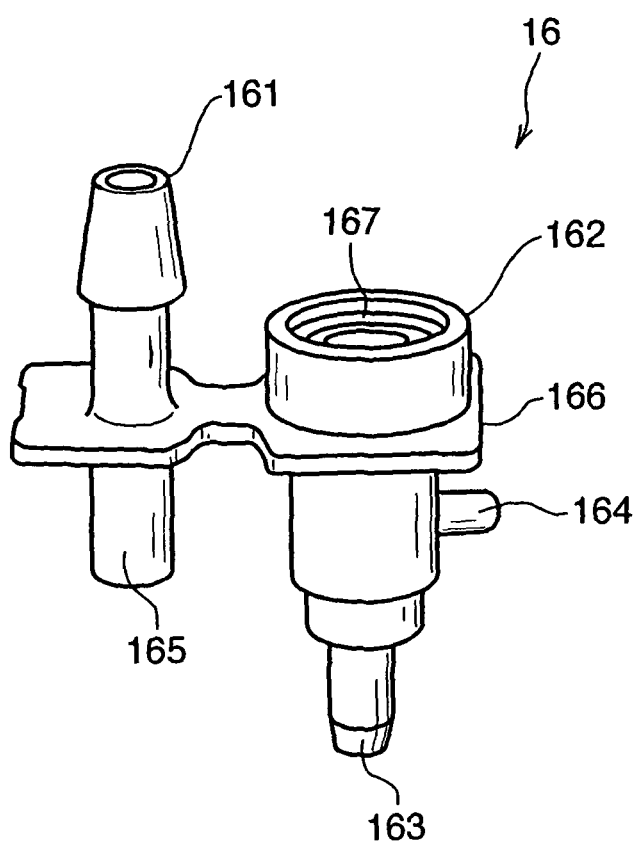
FIG. 6 depicts a connector for connecting a sphygmomanometer main body to a cuff tube.
Figure 7:
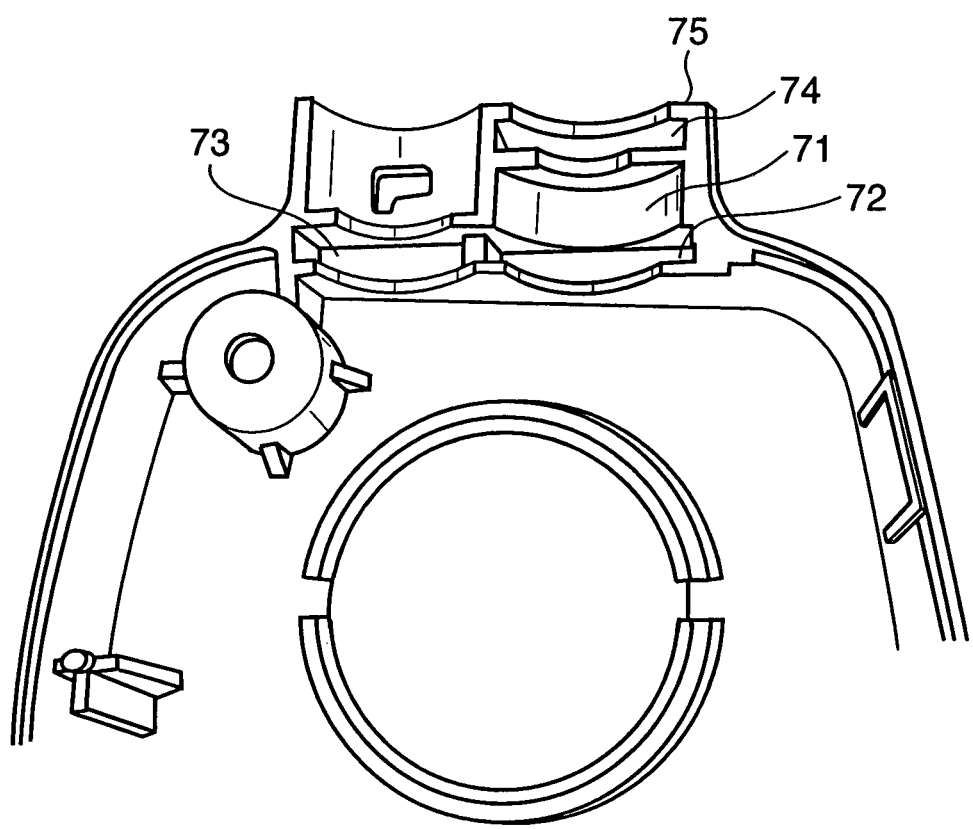
FIG. 7 depicts a portion of the sphygmomanometer main body that houses the connector in FIG. 6.
Figure 8:
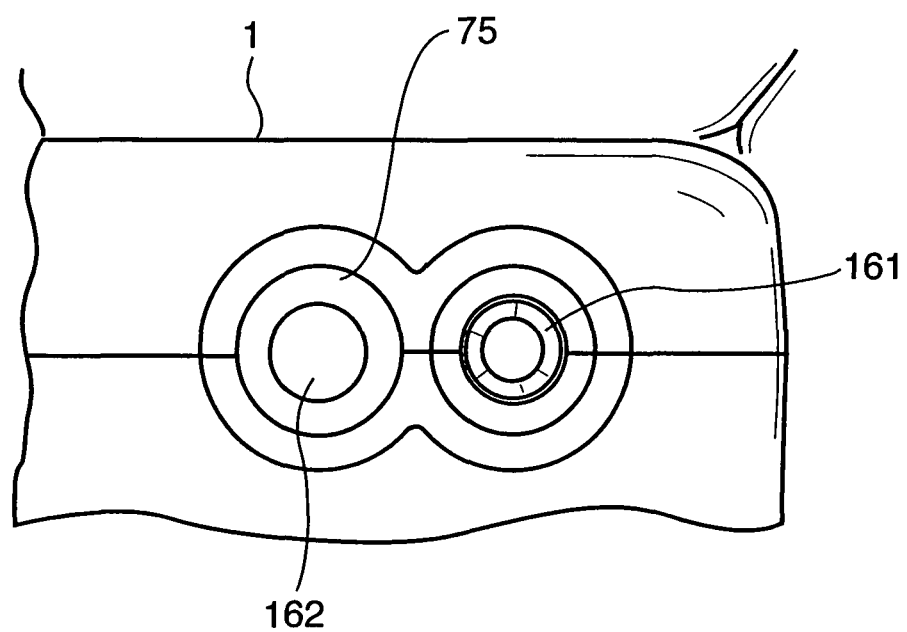
FIG. 8 depicts an external view of a portion that connects a sphygmomanometer and a cuff tube.
Figure 9:
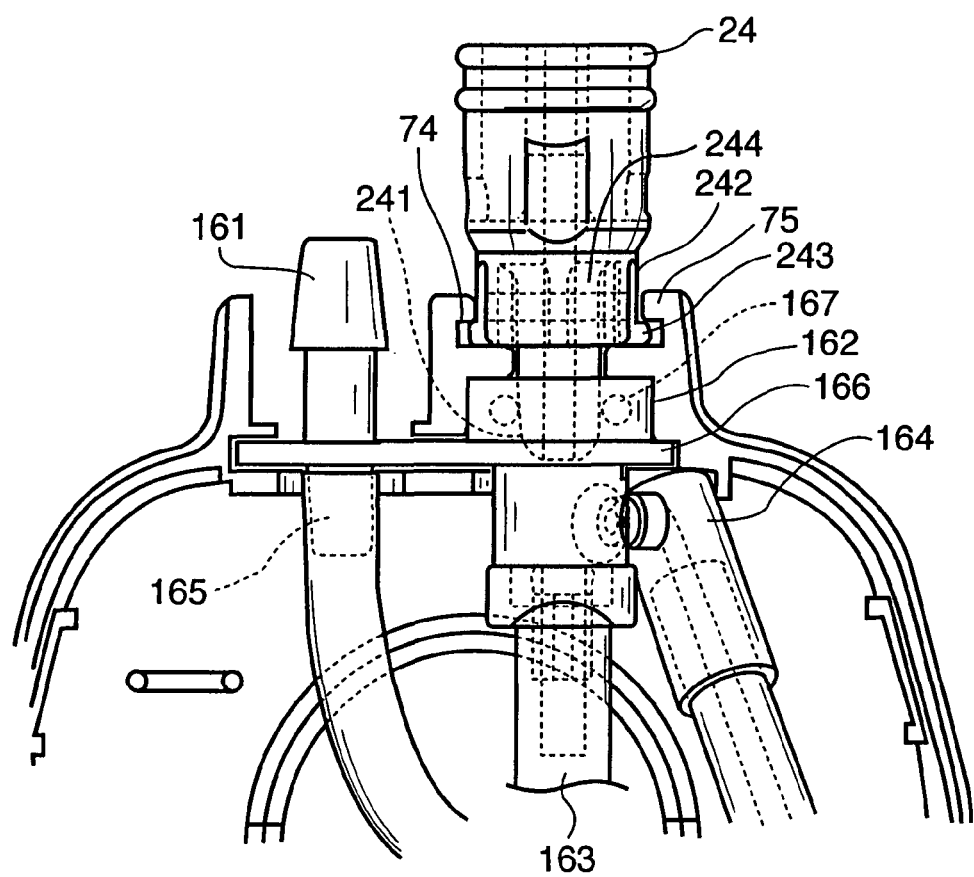
FIG. 9 depicts a connection of a cuff tube, i.e., a small cuff tube, to the sphygmomanometer main body.

FIGS. 6 through 8 are detailed depictions of a component that connects the cuff tubes 18 and 19 to the sphygmomanometer main body 1. FIG. 6 depicts the connector unit 16, FIG. 7 depicts an assembly of a connector unit within the sphygmomanometer main body 1, and FIG. 8 depicts a plan view of the component that connects to the cuff tube, when the component is housed within the sphygmomanometer main body 1. FIG. 9 is an enlarged view of the large cuff tube connector 24.

In FIG. 6, No. 161 is a large cuff male connector, and No. 162 is a small cuff female connector. No. 163 is a small cuff conduit connector unit, No. 164 is a pressure sensor conduit connector unit, and No. 165 is a large cuff conduit connector unit. No. 166 is a baseplate unit, which make the large cuff male connector 161 and the small cuff female connector 162 into a single unit. No. 167 is an o-ring fitted into the depression of the small cuff female connector 162.

In FIG. 7, No. 71 is a housing unit for the small cuff female connector 162, No. 72 is a housing unit for the baseplate unit 166 that is within the small cuff female connector, and No. 73 is a housing unit for the baseplate unit 166 that is within the large cuff male connector. A depression, or fastening, 74 in the connector unit within the sphygmomanometer main body is built in to fasten the tube connector 24. A protrusion 75 is also built therein, because the depression 74 is built therein.

The baseplate unit 166 of the connector unit 16 is housed within the housing unit 72 and 73 in FIG. 7, with a position determined such that the connector unit 16 neither shifts, nor becomes unsteady, within the sphygmomanometer main body 1. The cylindrical small cuff female connector 162 is housed within the small cuff female connector housing unit 71. Building a housing unit that is fitted to the shape of the connector unit 16 within the casing of the sphygmomanometer main body 1 allows avoiding unsteadiness on the part of the connector unit 16, as well as performance of connecting the cuff tube to the sphygmomanometer main body 1 in a stable fashion.

As depicted in FIG. 8, the connection unit of the sphygmomanometer main body 1 is formed by fitting the upper casing and the lower casing thereof. The tip portion of the large cuff male connector 161 protrudes from the sphygmomanometer main body 1 to an extent; refer to FIG. 9 for a view of the protrusion. The protrusion 75 forms a flange that surrounds the perimeter of the component wherein the tube connector 24 is connected to the small cuff female connector 162.

As depicted in FIG. 9, the tube connector 24 comprises a tip unit 241, for communicating air pressure that changes within the small cuff 23 to the sphygmomanometer main body, an elastic unit 242, for securing the tube connector 24 itself within the connection unit of the sphygmomanometer main body, and a protrusion 243, which is formed on the tip of the elastic unit 242, which in turn is constituted of a plurality of elements that are cut in the circumference of a portion of an external wall unit 244, which is formed so as to encompass the tip unit 241. When the tube connector 24 is connected to the small cuff female connector 162, the blade spring 243 fits into the depression 74, and the protrusion 243 and the protrusion 75 on the sphygmomanometer main body grip the tube connector 24, which makes it difficult for the tube connector 24 to come apart from the sphygmomanometer main body.

The interior of the small cuff female connector 162 contains the o-ring 167, which eliminates a gap that may emerge between the tip unit 241 and the small cuff female connector 162, thus avoiding air leaking therefrom.

When the protrusion 243 of the tube connector 24 is fitted into the depression 74 of the sphygmomanometer main body 1, the gauge that is regulated with the blade spring protrusion 243 is larger than the gauge that is regulated with the protrusion 75 of the sphygmomanometer main body, giving rise to a clicking sensation, owing to the resiliency of the elastic unit 242. The clicking sensation allows the user to easily determine that the tube connector 24 is connected to the sphygmomanometer main body 1.

<Assembly of Connection Unit for Air Supply Sphere 15 and Sphygmomanometer Main Body Casing 10>
(First Concrete Example Assembly)

Figure 10B:
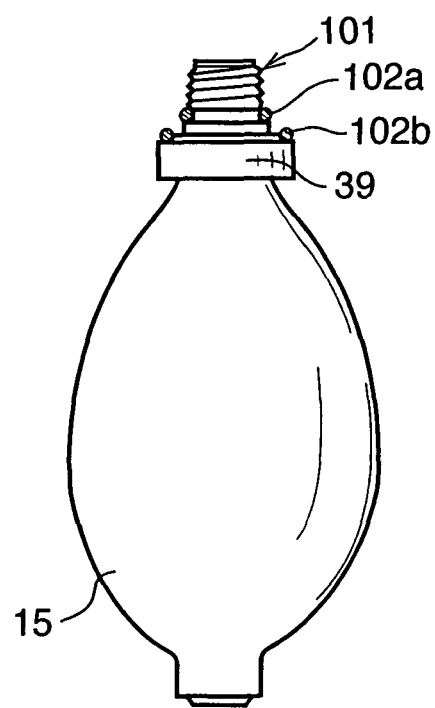
Figure 10C:
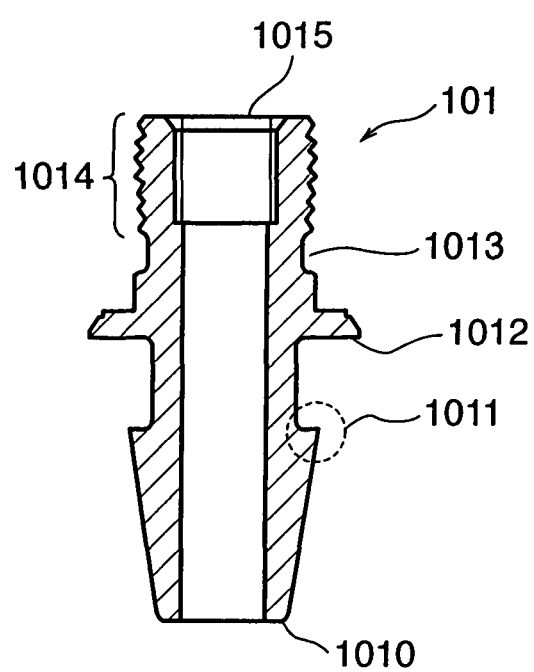

FIGS. 10A through 10C depict an assembly of a connection unit between an air supply sphere 15 and a sphygmomanometer main body casing 10. FIG. 10A depicts the air supply sphere 15 as fitted into the casing 10, FIG. 10B depicts the air supply sphere 15 when detached from the casing 10, and FIG. 10C is a cutaway enlargement of an air supply sphere connector.

In FIG. 10A, No. 101 is the air supply sphere connector, Nos. 102a and 102b are o-rings, No. 103 is a mesh dust filter, and No. 104 is a filter cap. A small diameter o-ring 102a has a sealing effect in a circumference direction, and a large diameter o-ring 102b has an effect of preventing slack by being compressed, or deformed, in an axial direction. Placing the two o-rings 102a and 102b provides the two effects.

As depicted in FIG. 10B, the air supply sphere connector 101 is fitted with a screw thread 1014, and fitting of the air supply sphere 15 is performed by screwing the air supply sphere connector 101 into the manifold 31.

The air supply sphere connector 101 is inserted into the air supply sphere 15 from an insertion unit 1010 to a flange unit 1012. The air supply sphere connector 101 is fitted with an expanded diameter step unit 1011, which provides resistance near the insertion point of the rubber air supply sphere 15, which makes it difficult for the air supply sphere 15 to come undone from the connector. The caulking ring 39, according to FIG. 10A, constricts near the insertion point of the rubber air supply sphere 15 from outside, making it even more difficult for the air supply sphere 15 to come undone from the air supply sphere connector 101. The expanded diameter step unit 1011 and the caulking ring 39 of the air supply sphere connector 101 secure the air supply sphere 15 and the air supply sphere connector 101 from within and without.

The peripheral outside of the air supply sphere connector 101 is formed of a depression 1013. As depicted in FIG. 10A, for example, the rubber o-rings 102a and 102b are fitted, forming a seal when the air supply sphere 15 is screwed into the manifold 31. The o-ring 102b serves to prevent slack when the air supply sphere 15 is screwed into the manifold 31.

The air supply sphere connector 101 possesses a filter mounting unit 1015, within which is mounted a filter cap 104, which is fitted onto the dust filter 103, which, in turn, is capable of preventing dust getting into components within the sphygmomanometer 1 that may include, but are not limited to, the conduits 33, 34, and 36, the electromagnetic valve 38, and the tubes 18 and 19 that lead to the cuff 2. It is thus possible to prevent the tubes being blocked, or a malfunction in the electromagnetic valve 38 or the pressure sensor 92. No. 1020 is a check valve.

(Second Concrete Example of Assembly)

Figure 12A:
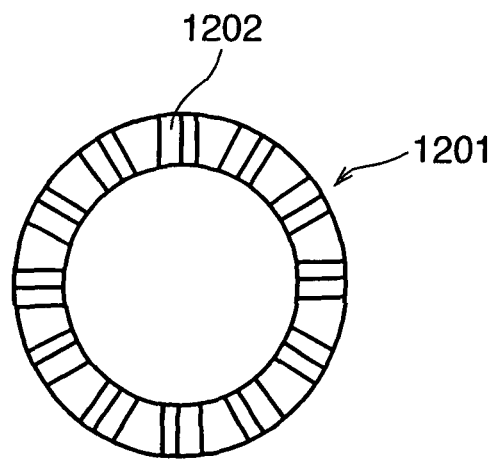
FIGS. 12A, 12B, and 12C depict an assembly of a one-way clutch ring on a connection unit between an air supply sphere 15 and the sphygmomanometer main body 10, pertaining to a connection unit between an air supply sphere 15 and the sphygmomanometer main body 10.
Figure 12B:
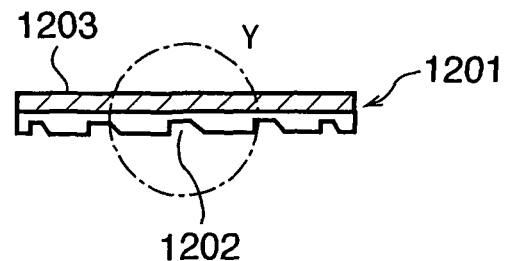
Figure 12C:
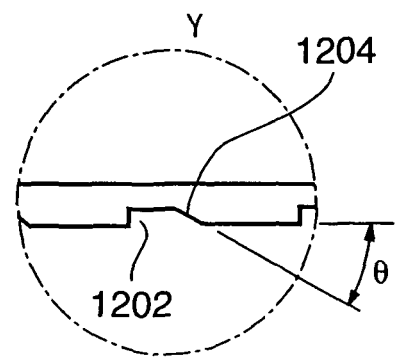

FIGS. 11A, 11B, and 11C and FIGS. 12A, 12B, and 12C depict a second concrete example of an assembly of a connection unit between the air supply sphere 15 and the sphygmomanometer main body casing 10. In particular, FIGS. 11A, 11B, and 11C depict a second concrete example of an assembly of the air supply sphere connector 101, and FIGS. 12A, 12B, and 12C depict a second concrete example of an assembly of a one-way clutch ring 1201.

Whereas in the first concrete example, the o-ring 102b was fitted into the depression 1013 of the air supply sphere connector 101, the one-way clutch ring 1201 is fitted in place of the o-ring 102 b in the second concrete example, as per FIGS. 12A and 12B.

As depicted in FIGS. 12A and 12B, the underside of the one-way clutch ring 1201 has, for example, 12 trapezoidal cutout units 1202, spaced at regular intervals. As depicted in the enlargement in FIG. 12C, the cutout units 1202, the angle of one end of a portion, signified by the "Y" in the diagram, is an outline right angle, whereas the other end has a slant, the angle of which forms a prescribed angle θ, between 15 and 30 degrees, for example. An elastic ring 1203, for example, a foam rubber ring, a sponge ring, a rubber ring, or the like, is adhered to the upper side of the one-way clutch ring 1202. The effect of the elastic ring 1203 is described hereinafter.

As depicted in FIG. 11A, the flange unit 1012 of the air supply sphere connector 101 has, for example, four trapezoidal protrusion units 1102, spaced at regular intervals. As depicted in the enlargement in the portion marked X in FIG. 11B, the angle of one end of a portion is an outline right angle, whereas the other end has a slant, the angle of which forms a prescribed angle θ, between 15 and 30 degrees, or in other words, the same angles as the angles of the cutout units 1202. Accordingly, the relationship between the trapezoidal protrusion units 1102 and the trapezoidal cutout units 1202 is such that they fit together precisely.

The one-way clutch ring 1201, with the preceding assembly, is fitted into a step unit 1103 of the air supply sphere connector 101. The air supply sphere 15 is screwed into the manifold 31 such that the trapezoidal cutout units 1202 of the one-way clutch ring 1201 and the trapezoidal protrusion units 1102 of the air supply sphere connector 101 are fitted together. When the air supply sphere 15 approaches a state of being tightly fitted into the manifold 31, the elastic ring 1203 of the one-way clutch ring 1201 makes contact with the interior surface of the manifold 31, and the resulting friction restrains the rotation of the elastic ring 1203. The air supply sphere 15 is screwed in, and a slanted portion 1103 of the trapezoidal protrusion units 1102 of the air supply sphere connector 101 overtops a slanted portion 1204 of the trapezoidal cutout units 1202 of the one-way clutch ring 1201, making a clicking sound. When the screwing of the air supply sphere 15 into the manifold 31 is complete, the elastic ring 1203 is deformed, thus preventing the one-way clutch ring 1201 from spinning to no purpose, while also securing the air supply sphere 15 firmly within the sphygmomanometer main body 1.

<Details of Display Unit 11>

Figure 13:
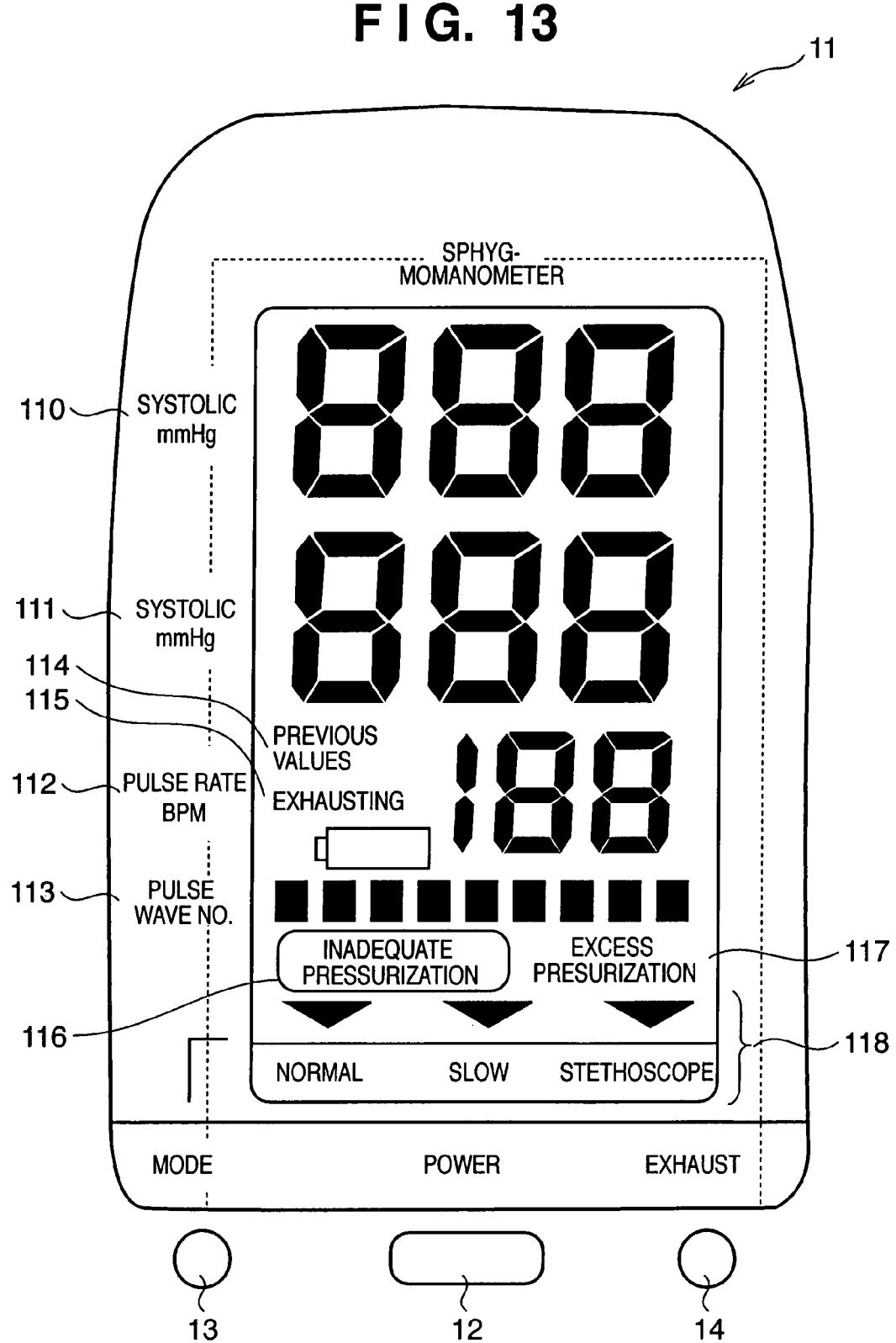
FIG. 13 depicts a concrete example of a sphygmomanometer display unit.

FIG. 13 depicts details of the display unit 11 of the sphygmomanometer 1.

In FIG. 13, No. 110 is a systolic blood pressure display, No. 111 is a diastolic blood pressure display, No. 112 is a pulse rate display, No. 113 is a pulse wave signal display, No. 114 is a previous value display, No. 115 is an exhaust display, No. 116 is an inadequate pressurization display, No. 117 is an excess pressurization display, and No. 118 is a display of which mode is currently being selected.

The systolic blood pressure display 110 displays pressure at any instance when both pressurizing and depressurizing, ultimately displaying the systolic blood pressure. The diastolic blood pressure display 111 displays the ultimately determined diastolic blood pressure. For example, if diastolic blood pressure is determined to be 80, operation wherein exhaust and depressurization at the same speed as that used up to that point is pointless, and thus, the electromagnetic valve 36 is controlled such that exhaust proceeds at high speed starting at pressure value 60. During high speed exhaust, the exhaust display 115 flashes on and off. The exhaust display 115 flashes on and off even when the exhaust switch 14 is pressed. In such circumstance, the electromagnetic valve is controlled to be forcibly released and exhaust at high speed. Exhaust speed during high speed exhaust is not less than double that during regular depressurization. The pulse rate display 112 displays the measured pulse rate. The previous value display either flashes or lights steadily when the power switch 12 is pressed, and displays the systolic and diastolic blood pressure, as well as the pulse rate, that were measured in the most recent measurement, on the systolic blood pressure display 110, the diastolic blood pressure display 111, and the pulse rate display 112, respectively. After a brief interval, or when air supply from the air supply sphere 15 commences, the display lights go out, as does the flashing or steadily lit previous value display. A circumstance may also arise wherein the pressure instantaneously increases during pressurization, i.e., instantaneous pressure increases, and if the raw instantaneous pressure data is displayed in the display unit, it is possible that a user may mistakenly conclude that sufficient pressure is present. According to the embodiment, user confusion is avoided by having the display unit, i.e., the systolic blood pressure display 110, display a blunted pressure data, rather than displaying the instantaneous pressure data.

The pulse wave signal display 113 shows the size of the detected pulse wave signal, in a bar display. Whereas the bar will increase and decrease rhythmically from left to right and back again for a person being measured who has a typical pulse, the bar will not move rhythmically for a person being measured who has an irregular pulse. Installing the pulse wave signal display 113 is thus highly useful, as it allows a visual determination of whether the person being measured has an irregular pulse or not.

When the inadequate pressurization display 116 is lit or is flashing, it means that pressure within the cuff 2 has not reached a level sufficient for measurement, and motivates the user to use the air supply sphere to supply air. When the excess pressurization display 117 is lit or is flashing, it means that pressure within the cuff 2 is at or above a prescribed pressure, for example, 320 mmHg or more, and motivates the user to look thereat and stop the pressurization operation.

The display of which mode is currently being selected 118 shows which mode has been selected using the mode switch 13. It displays which mode is selected, from among Normal, Slow, and Stethoscope. According to the embodiment, the display is made such that a black inverted triangle mark that is positioned above the mode display that is printed on the cover of the sphygmomanometer main body will either light or flash.

The mode selection allows changing speed of exhaust, or depressurization. When Normal Mode is selected, exhaust speed is configured, for example, to 5±αmmHg/sec. Normal Mode has an advantage of being comparatively shorter measurement time, as it has comparatively faster exhaust speed. On the other hand, pressure fluctuation measurement interval also increases, which, while posing no particular problem when measuring a person with a stable pulse rate, it may increase measurement error when measuring blood pressure of a person with an irregular pulse rate, as a pulse may be easily missed. According to the embodiment, a Slow Mode is built in, and when Slow Mode is selected, the air supply rate is set to approximately half that of Normal Mode, for example, 2.0-2.5 mmHg/sec. Slow Mode thus allows viewing pressure change to be viewed in greater detail by depressurizing more slowly than normal, allowing more accurate performance of measurement of a person with an irregular pulse rate, who has a pulse that may be easily missed. Stethoscope Mode uses a stethoscope for manual measurement, which is also configured to exhaust at approximately half the speed of Normal Mode, for example, 2.0-3.0 mmHg/sec.

According to the embodiment, a cuff size ranging from XS to XL is provided, and it is important that exhaust speed not be affected by cuff size. The opening and closing of the electromagnetic valve 38 is controlled, i.e., with feedback control, such that the bigger the cuff size, the bigger the air capacity that is exhausted per second.

While not shown in the drawings, pressing the power switch 12 while pressing the mode switch 13, and holding down the mode switch 13 for at least one second, will change the display to the number of measurements. In such circumstance, the systolic blood pressure display 110 displays that the display is showing the number of measurements, and the diastolic blood pressure display 111 displays the number of measurements, which may be made to display only in units of 100 or more, and to not display in units of 10 or less.

<Sphygmomanometer Control Circuit Block Diagram>

FIG. 14 depicts a control circuit block diagram of the sphygmomanometer 1.

In FIG. 14, No. 91 is a control unit for controlling the circuit overall, for example, a CPU, and No. 92 is a pressure sensor for detecting the pressure of the cuff 2, both the large cuff 22 and the small cuff 23. No. 93 is a ROM that stores a control program and various types of data, and No. 94 is a RAM that temporarily stores a computation result or a measurement result. No. 95 is a drive unit for driving the electromagnetic valve 38 in accordance with a control signal from the control unit 91, and No. 96 is a buzzer that makes a prescribed warning. No. 97 is a battery power supply, and No. 98 is a power control unit for controlling the battery power supply.

First, the user presses the power switch 12, then uses the mode switch 13 to select a mode. A display operation of the display unit 11 for the pressing of the power switch 12 and the mode selection are as previously described.

Air from the air supply sphere 15 passes through the manifold 31, and is sent to the large cuff 22 via the manifold junction 32, the large cuff conduit 33, and the large cuff tube 18. A portion of the air from the air supply sphere is also supplied to the small cuff 23 via the bypass tube 34, the conduit junction 35, and the small cuff tube 19.

Air that branches off via the conduit junction 35 is supplied to the pressure sensor 92 via the pressure sensor conduit 36. During such circumstance, i.e., during pressurization, a pressure fluctuation value detected by the pressure sensor 92 is very large compared with a pressure fluctuation value during measurement, i.e., depressurization. Consequently, if the detected pressurization fluctuation value meets or exceeds a prescribed value, the control unit 91 determines that pressurization is currently underway, and outputs a control signal that directs the drive unit 95 to close the electromagnetic valve 38. Upon receipt of the control signal, the drive unit 95 closes the electromagnetic valve 38, keeping air from leaking out of the electromagnetic valve 38. The air supply sphere 15 and the pressure sensor 92 are connected by the bypass tube 34, which is thinner than the large cuff conduit 33, which has the effect of blunting drastic pressurization. If the pressure increases drastically, there is a risk that a large pressure value will be displayed in the display unit 11, and a user may mistakenly assume that sufficient pressure has been achieved. Accordingly, it is possible to avoid such a mistaken assumption on the part of the user, by blunting a pressure change.

The buzzer 96 issues a sound in an instance that may include, but is not limited to, when the power to the sphygmomanometer main body is switched on and the display unit is activated, when the mode is changed via the mode switch 13, when the blood pressure value is determined, or when an error occurs.

The user views the value that is shown in the systolic pressure display of the display unit 11, decides whether the pressurization in the large cuff 22 and the small cuff 23 is sufficient for measuring, and if the pressurization is determined to be sufficient, it stops air being supplied from the air supply sphere 15. In such circumstance, the pressure sensor 92 detects that the pressure fluctuation value, i.e., the increase value, is effectively zero or in a depressurization state, within a prescribed time interval. The control unit 91 outputs a control signal that directs the drive unit 95 to open the electromagnetic valve 38, and upon receipt of the control signal, the drive unit 95 opens the electromagnetic valve 38 such that depressurization speed reaches a prescribed value. The operation of the sphygmomanometer switches from pressurization mode to measurement mode.

When in measurement mode, the systolic blood pressure and the diastolic blood pressure are measured according to a measurement program that is stored in the ROM 93. Determination operation of blood pressure value, etc., are described in detail with reference to the flowchart in FIG. 17, and thus, only an overview will be presented for the present.

When air that is supplied to the large cuff 22 is gradually exhausted to the outside according to depressurization, blood flow that has been impeded commences at a given point in time. The commencement of blood flow gives rise to a fluctuation in pressure within the small cuff 23. The fluctuation in pressure is detected by the pressure sensor 92, and is treated as the point at which the building of a pulse wave signal is detected. A successive pressure value vis-à-vis the detection of the pulse wave is stored sequentially as a measured value in the RAM 94. The pressure value of the point at which the building of a pulse wave signal is detected or the successive pressure value that is stored sequentially are used in determining the systolic blood pressure and the diastolic blood pressure, as described hereinafter.

The pulse value is determined by detecting a number of pulses over a prescribed time interval, and converting to a number of pulses in a 60-second period.

<Systolic Blood Pressure and Diastolic Blood Pressure Determination Operation>

Figure 15:
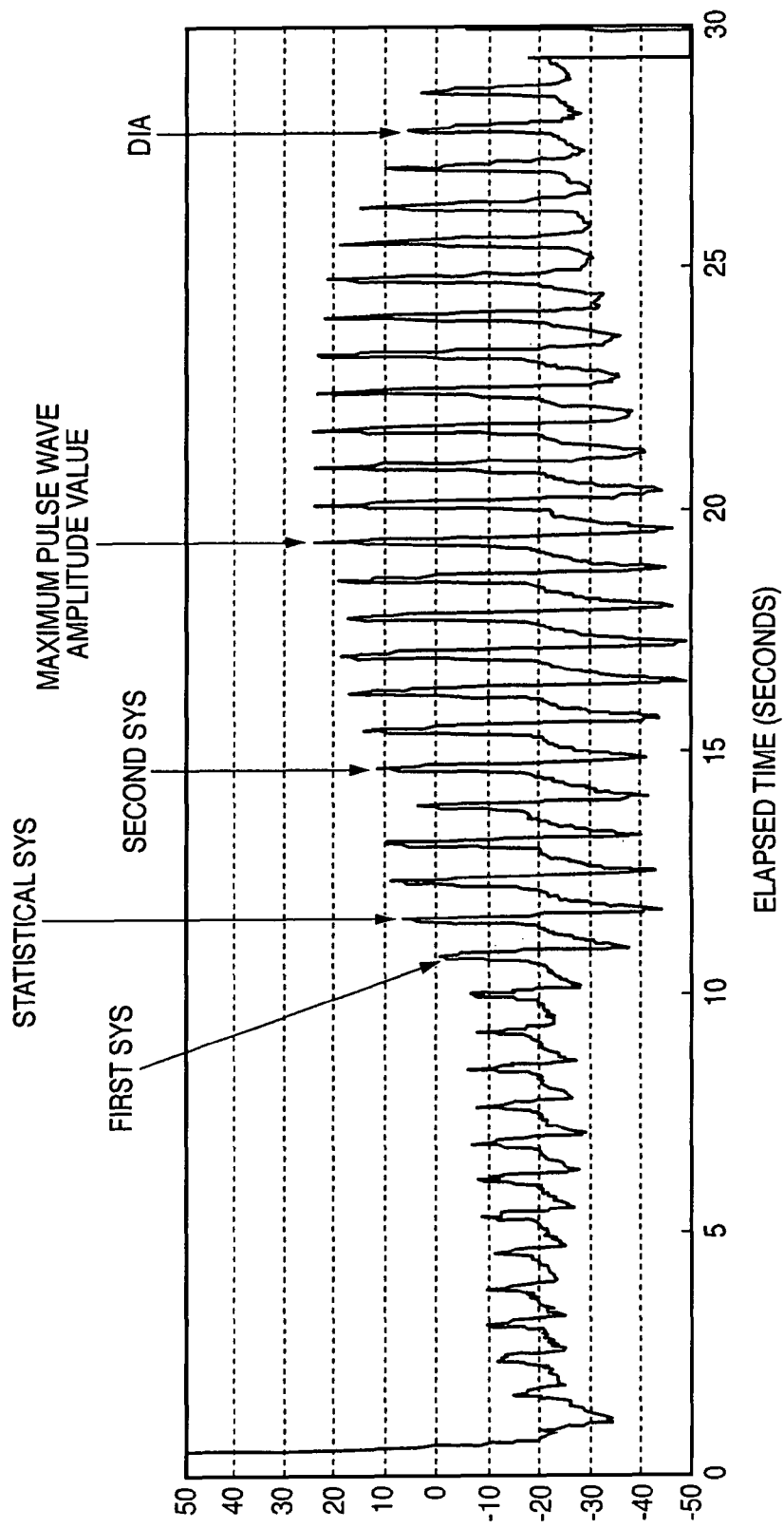
FIG. 15 is a graph depicting a pressure change when pressure declines.
Figure 16:
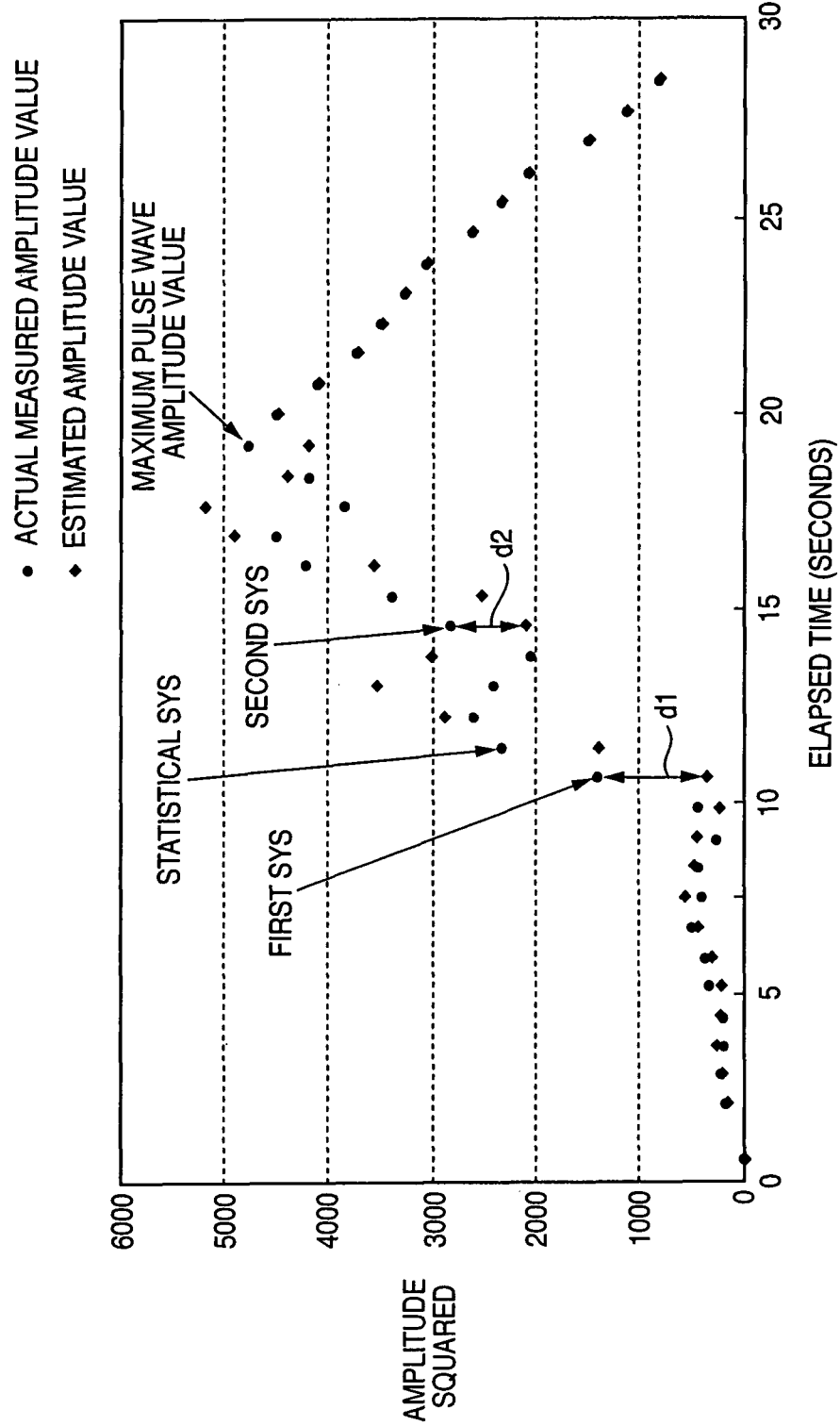
FIG. 16 is a graph depicting an estimated measured value and an actual measured value of a pressure change when pressure declines.
Figure 17:
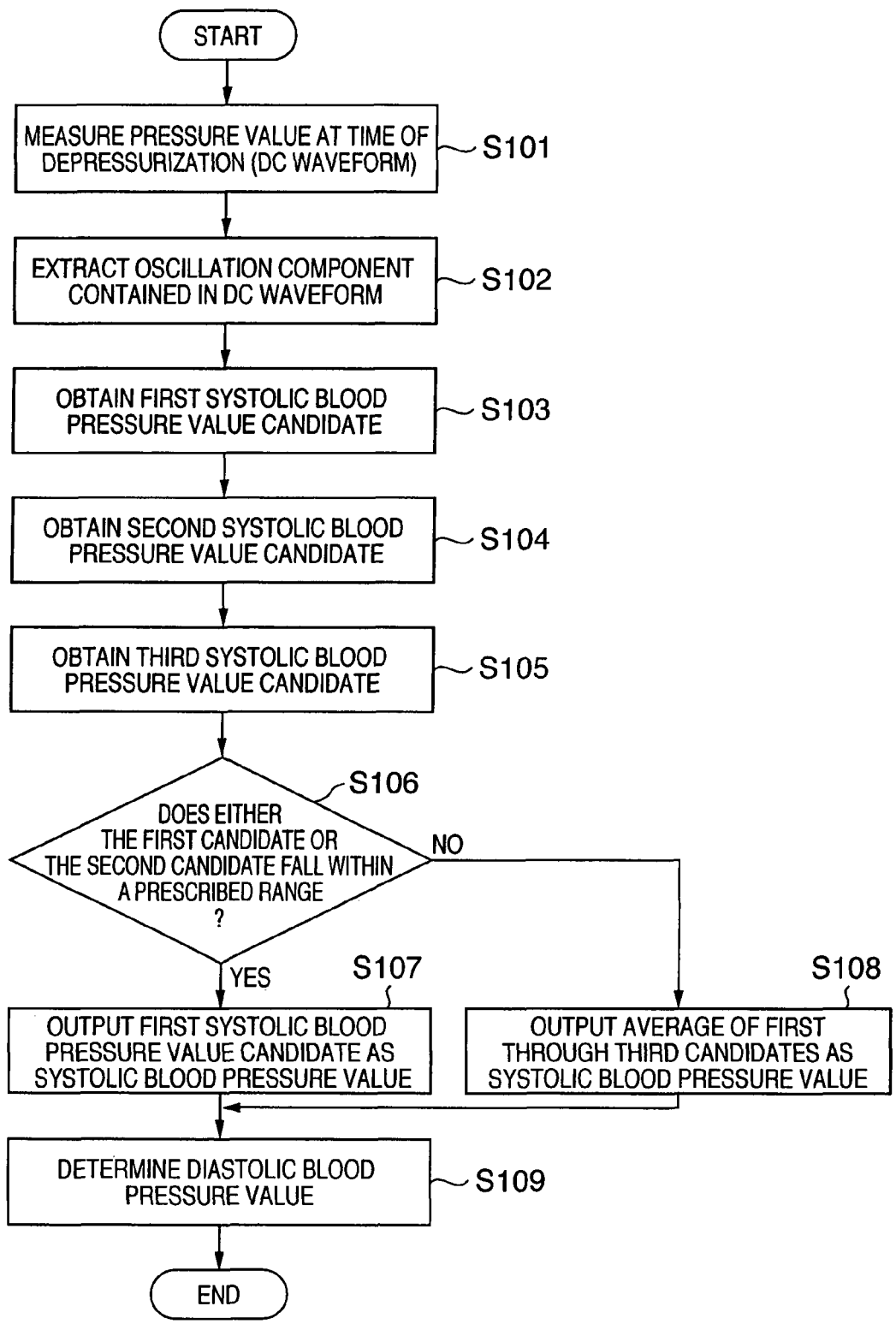
FIG. 17 is flowchart describing an operation that determines systolic and diastolic pressure.

The following section describes the operation that determines systolic and diastolic blood pressure, with reference to FIGS. 15 through 17. FIG. 15 is a graph depicting a pressure change when pressure declines, FIG. 16 is a graph depicting an estimated measured value and an actual measured value of a pressure change when pressure declines, and FIG. 17 is flowchart describing the operation that determines systolic and diastolic pressure.

In the flowchart in FIG. 17, the pressure value at time of depressurization, i.e., the DC waveform, is measured in step S101. The pressure value at time of depressurization is shown in the graph in FIG. 15. While there are locations within the graph wherein the pressure value changes drastically, they depict a change that occurs upon rapid exhaust following determination of the diastolic blood pressure value and a passing of a prescribed time interval. The respective measured pressure values are temporarily stored in the RAM 94. It is assumed that a time t=0 when supply of air is completed.

In step S102, an oscillation constituent, i.e., a fluctuation value, or AC constituent, that is contained within a pressure that is measured at time of depressurization, is extracted, and the extracted value is stored within the RAM 94. The oscillation constituent is extracted by filtering the pressure value. A graph of the extracted oscillation constituent is similar to that shown in FIG. 15.

In step S103, a first candidate point for a systolic blood pressure value, i.e., a first SYS, is obtained, in accordance with the oscillation property obtained in step S102. During a prescribed time interval from the commencement of depressurization, the oscillation constituent is very slight, owing to blood being trapped, by the large cuff 21, in the arm of the person being measured. When blood flow recommences according to reduction of pressure within the large cuff 21, there is a point of an initial dramatic build-up, i.e., the first SYS in FIG. 15. When a difference d1 between an actual measured amplitude value and an estimated amplitude value of the point of build-up are within a prescribed range, for example, between 5% and 15%, of maximum pulse wave amplitude value, wherein actual measured amplitude value is greater than estimated amplitude value, the blood pressure value, i.e., the DC value, corresponding to the point is treated as the first candidate point for the systolic blood pressure value. The 15% is assumed because it is highly possible, with a larger difference, that the value is abnormal. As depicted in FIG. 16, the estimated amplitude value is estimated from a temporally previous point, for example, the point that is three points prior to the present. "Candidate" in the present circumstance is by no means limited to the pressure value at the initial build-up point signifying the systolic blood pressure value, as there would be a disturbance in the pulse wave if, for example, the person whose blood pressure is being measured has an irregular pulse. Accordingly, consideration is also given to a candidate value that is obtained with a different method, according to the embodiment.

In step S104, a second candidate point for a systolic blood pressure value, i.e., a second SYS, is obtained, in accordance with the oscillation property obtained in step S102. The second SYS is a point of dramatic decline as seen from the maximum pulse wave amplitude value, and, as per FIG. 16, a difference d2 between an actual measured amplitude value and an estimated amplitude value, wherein actual measured amplitude value is greater than estimated amplitude value, is taken to be a point that falls within 5 and 15% of the initial maximum pulse wave amplitude value, as seen from the maximum pulse wave amplitude value point. A blood pressure value, i.e., a DC value, which corresponds to the second SYS is treated as a second candidate for the systolic blood pressure value.

In step S105, a third candidate point for the systolic blood pressure value, i.e., a statistical SYS, is obtained, which is a point that falls within a prescribed proportion of the maximum pulse wave amplitude value, and that forms a basis for experimental probability. Accordingly, the statistical SYS is valid when there is a plurality of build-up points, and it is unclear as to which is probable.

In step S106, if the difference between the first candidate for the systolic blood pressure value, corresponding to the first SYS, and the second candidate for the systolic blood pressure value, corresponding to the second SYS, is within a prescribed value, in mmHg, the process proceeds to step S107, wherein the first candidate for the systolic blood pressure value is determined to be the systolic blood pressure value.

If the difference falls outside a prescribed range, the process proceeds to step S108, wherein, for example, the average of the first through third candidates for the systolic blood pressure value is determined to be the systolic blood pressure value. It is permissible to apply weighting to the three values as well.

In step S109, diastolic blood pressure value is computed. As is clear from FIG. 15, while the envelope becomes progressively smaller from the maximum pulse wave amplitude value, the point where it reaches the prescribed proportion of the maximum pulse wave amplitude value is taken as the point that depicts the diastolic blood pressure value, i.e., the DIA, and the blood pressure value, i.e., the DC value, is determined to be the diastolic blood pressure value. It is not absolutely necessary to execute computation of the determination of the diastolic blood pressure value after determination of the systolic blood pressure value; rather, it may executed prior, or in parallel, thereto as well.

The systolic and diastolic blood pressure values thus derived are displayed in the display unit 11.

Whereas, in the present circumstance, if the difference between the first candidate for the systolic blood pressure value and the second candidate for the systolic blood pressure value falls outside the prescribed range, the average of the first through third candidates for the systolic blood pressure value is taken to be the systolic blood pressure value, it is also permissible for the average of the first and third candidate values, or the third candidate value, to be taken to be the systolic blood pressure value. It is also permissible for the average of the first and third candidate values to be taken to be the systolic blood pressure value, regardless of whether or not the difference between the first candidate for the systolic blood pressure value and the second candidate for the systolic blood pressure value falls within the prescribed range. It is further permissible to derive the first and second candidate values, and take the average thereof to be the systolic blood pressure value.

Figure 23A:
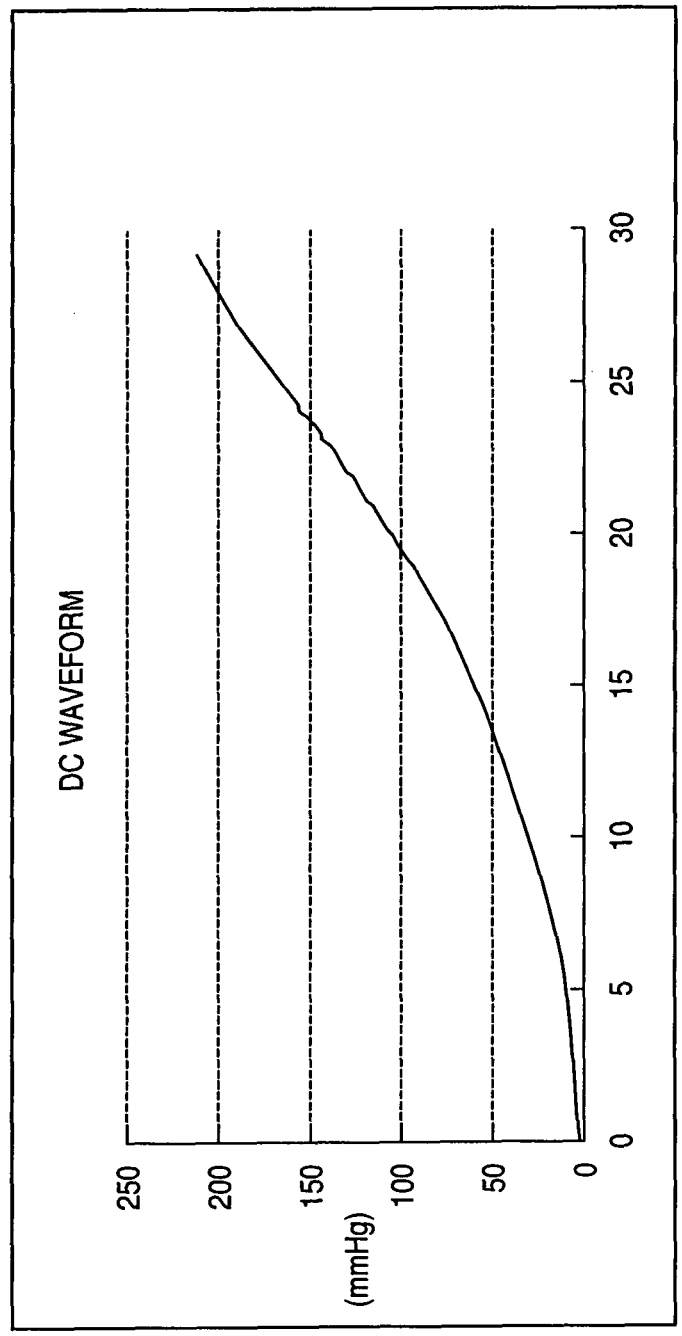
FIGS. 23A and 23B are graphs depicting a pressure change when pressure increases.
Figure 23B:
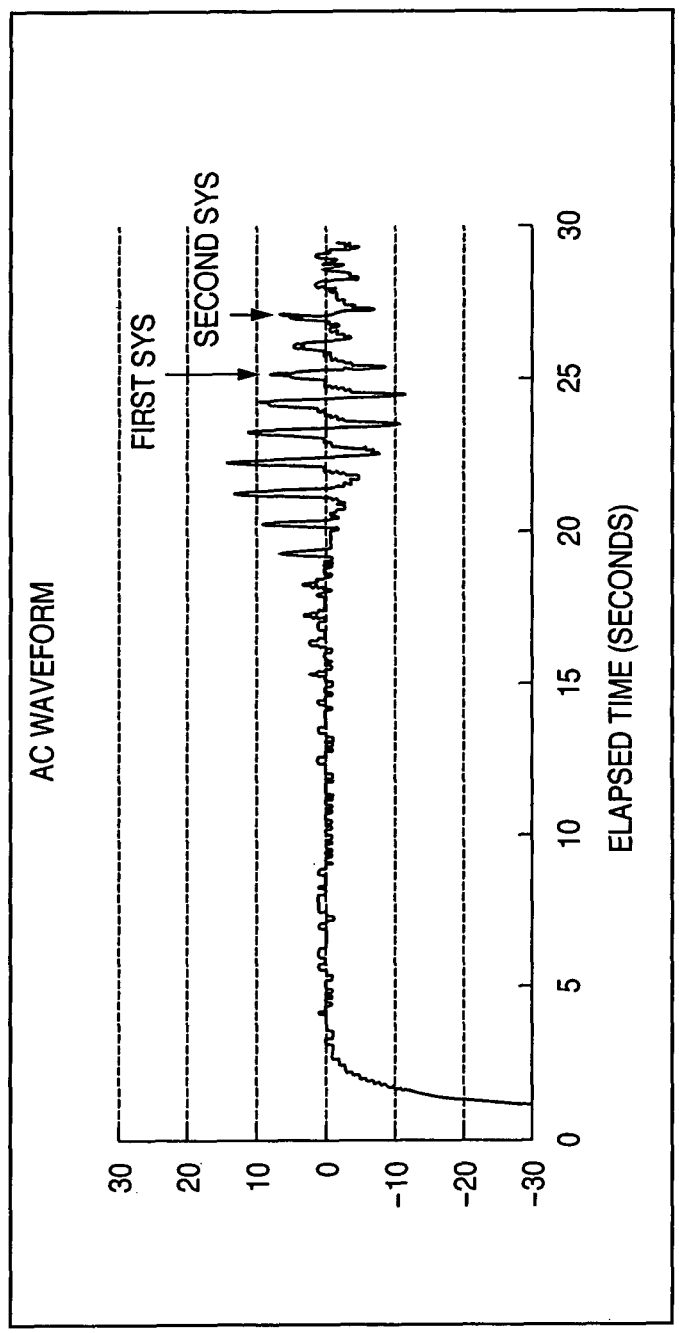

Whereas, according to the embodiment, unless otherwise-specified, a plurality of build-up points are detected and a systolic blood pressure value ultimately derived as a systolic blood pressure value candidate, it is also permissible to use the algorithm depicted in the flowchart in FIG. 17 to determine the systolic blood pressure value and the diastolic blood pressure value, instead. While the property of pressure fluctuation at time of depressurization is as per FIG. 15, the systolic blood pressure value is obtained by the same algorithm, as depicted in FIGS. 23A and 23B, deriving the property of pressure fluctuation at time of pressurization, i.e., increasing pressure, and detecting a plurality of systolic blood pressure value candidates, i.e., the first SYS, the second SYS, etc., as per the figures.

<Assembly and Operation of the Electromagnetic Valve 38>

An assembly and operation of the electromagnetic valve 38 that is used according to the embodiment is described hereinafter with reference to FIG. 18 through FIG. 22. Opening and closing operation of the electromagnetic valve 38 is PWM controlled.

Figure 18:
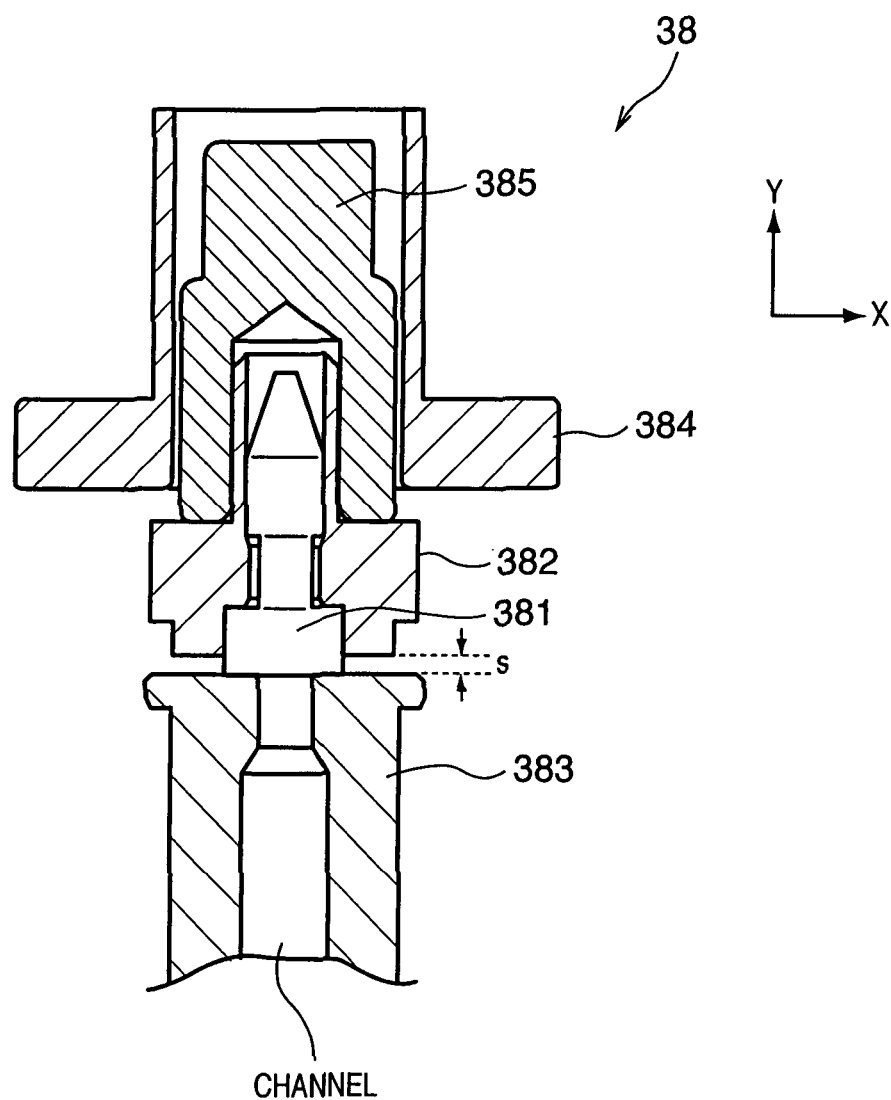
FIG. 18 depicts an assembly of an electromagnetic valve 38 that is used in a sphygmomanometer.

FIG. 18 depicts an assembly of the electromagnetic valve 38 that is used according to the embodiment. In FIG. 18, No. 381 depicts a rubber valve, No. 382 a first plunger, No. 383 a plunger receptacle, No. 384 a spacer, and No. 385 a second plunger, respectively.

The rubber valve 381 protrudes from the first plunger only to the extent of a space S. The rubber valve 381 prevents air from leaking from the electromagnetic valve 38, during pressurization, for example, by sealing a channel of the plunger receptacle 383. The rubber valve 381 facilitates exhaust, during depressurization, for example, by withdrawing from the plunger receptacle 383 and releasing the channel. The plunger receptacle 383 and the first and second plungers 382 and 385 are formed of a conductive metal. A voltage is applied to both ends of the electromagnetic valve 38, an electromagnetic force acts between the metallic plunger 382 and the plunger receptacle 383, and the greater the impressed voltage, for example, from 1.2 volts to a maximum of 1.7 or 1.8 volts, the greater the size of the electromagnetic force.

Figure 19:
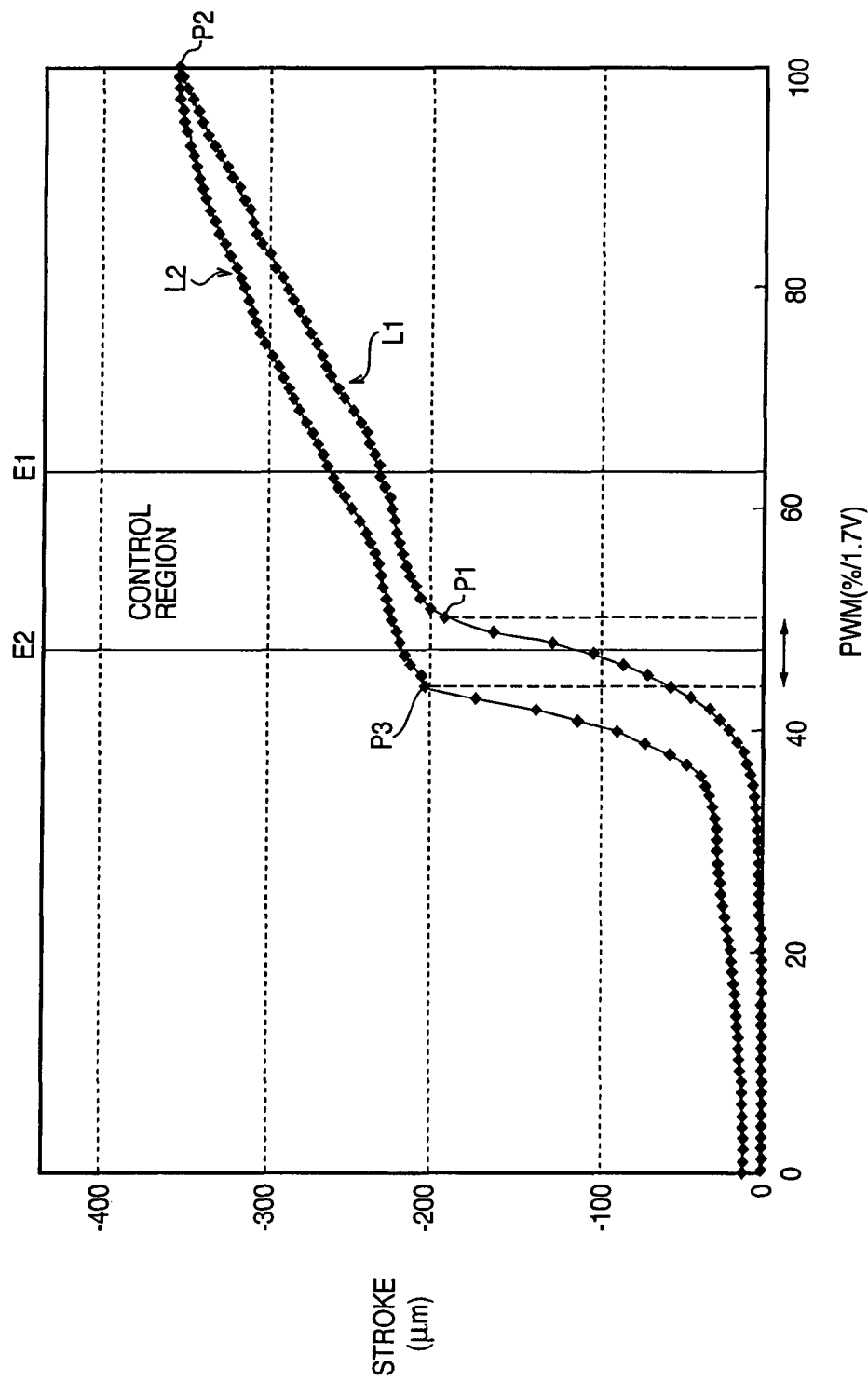
FIG. 19 is a hysteresis property that depicts a relationship between an applied voltage and a switching stroke as pertains to an opening of the electromagnetic valve 38 under normal circumstances.

FIG. 19 is a graph that depicts a hysteresis property when an opening and closing operation of the electromagnetic valve 38 is performed under normal circumstances. In the graph in FIG. 19, the horizontal axis depicts the voltage being impressed upon the electromagnetic valve 38, when PWM control is being performed, and expressed as a percentage, and the vertical axis depicts the valve release stroke, with zero signifying the valve being fully opened. In FIG. 19, a curve L1 depicts the hysteresis when closing the electromagnetic valve 38, and a curve L2 depicts the hysteresis when opening the selfsame valve.

When a voltage is gradually impressed, beginning when the electromagnetic valve 38 is fully opened, as per the curve L1, the electromagnetic valve 38 gradually begins to close at a point where the PWM reaches approximately 40%. When a point P1 is reached, wherein the PWM approaches approximately 50%, the channel is closed by the rubber valve 381, i.e., the release stroke approaches approximately −195 μm. At such point in time, the rubber valve 381 is still in a state of not being completely closed, and air is escaping. If further voltage is impressed, the channel is completely sealed by the flexible rubber valve being deformed. The stroke at the point in time of complete seal, i.e., a point P2, is approximately −340 μm.

When releasing the electromagnetic valve 38, i.e., curve L2, from the completely sealed state, i.e., P2, the impressed voltage is gradually lowered. The deformed rubber valve 381 returns to its original shape according to the fall in impressed voltage, and air escapes through a gap between the rubber valve 381 and the plunger receptacle 383, as the rubber valve 381 penetrates a right-hand edge of a control region E1. The electromagnetic valve 38 is in a semi-open state, and when the impressed voltage, i.e., the PWM, drops, the volume of air escaping through the gap increases commensurately. The electromagnetic valve 38 is fully open at a point P3, wherein the PWM is approximately 44%, and the release stroke is approximately −200 μm. Depressurization speed is controlled to be 5 mmHG/second according to the embodiment, and the control is executed within the control region as per FIG. 19.

In the present circumstance, the control region is a region bounded by E1 and E2, and is the region wherein exhaust is controlled with a depressurization speed of 5 mmHg/second. Voltage that corresponds to the control region is taken to be electromagnetic valve control voltage, i.e., between approximately 0.6 and approximately 1.0 volts, or between approximately 50% and approximately 64% PWM, for example, according to the embodiment. Whereas depressurization speed does not immediately reach 5 mmHg/second at the point in time of penetrating into the control region, i.e., PWM=E1, it is the point in time at which control commences in the direction of the given depressurization speed, and at which exhaust commences. Whereas the rubber valve 381 opens as impressed voltage drops, impressed voltage is controlled so as to achieve and maintain a depressurization speed of 5 mmHg/second. As depressurization proceeds, pressure within the cuff 2 drops, and the degree of opening of the rubber valve increases as well. When a left-hand edge of the control region, i.e., PWM=E2, is reached, control to maintain a depressurization speed of 5 mmHg/second ends, and rapid exhaust is executed. At such time, the cuff 2 pressure is configured to 20-30 mmHg, for example.

Force that maintains the closure state of the electromagnetic valve 38 between the points P1 and P2, and the points P2 and P3, is electromagnetic force from impressed voltage between the first plunger 382 and the plunger receptacle 383. Accordingly, a change in the release stroke between the points P2 and P3 is mild, whereas a change in the release stroke is more dramatic after release, i.e., after the point P3, as there is no more effect from electromagnetic force.

According to the embodiment, an electromagnetic valve is used whose opening and closing operation is controlled by impressed voltage, and thus, it is possible to close the electromagnetic valve 38 rapidly when sending air from the air supply sphere 15, i.e., during pressurization, and it is also possible to exhaust air within the cuff 2 in a stable manner when exhausting, i.e., during depressurization, as per the foregoing mode.

In order to perform the opening and closing operation in a stable manner, however, it becomes important to achieve a movement in the direction of the Y-axis, while the rubber valve 381 and the first plunger 382 are maintained in a horizontal orientation, as depicted in FIG. 18. Accordingly, when the electromagnetic valve 38 tilts, which may easily occur, as depicted in FIG. 20, a negative effect occurs in that the first plunger 382 and the plunger receptacle 383 will make contact, the electromagnetic force between the two metals will bond the two metals together, and the electromagnetic valve 38 will not be released even if a voltage is impressed, i.e., at point P3, that would otherwise release the electromagnetic valve 38.

Figure 21:
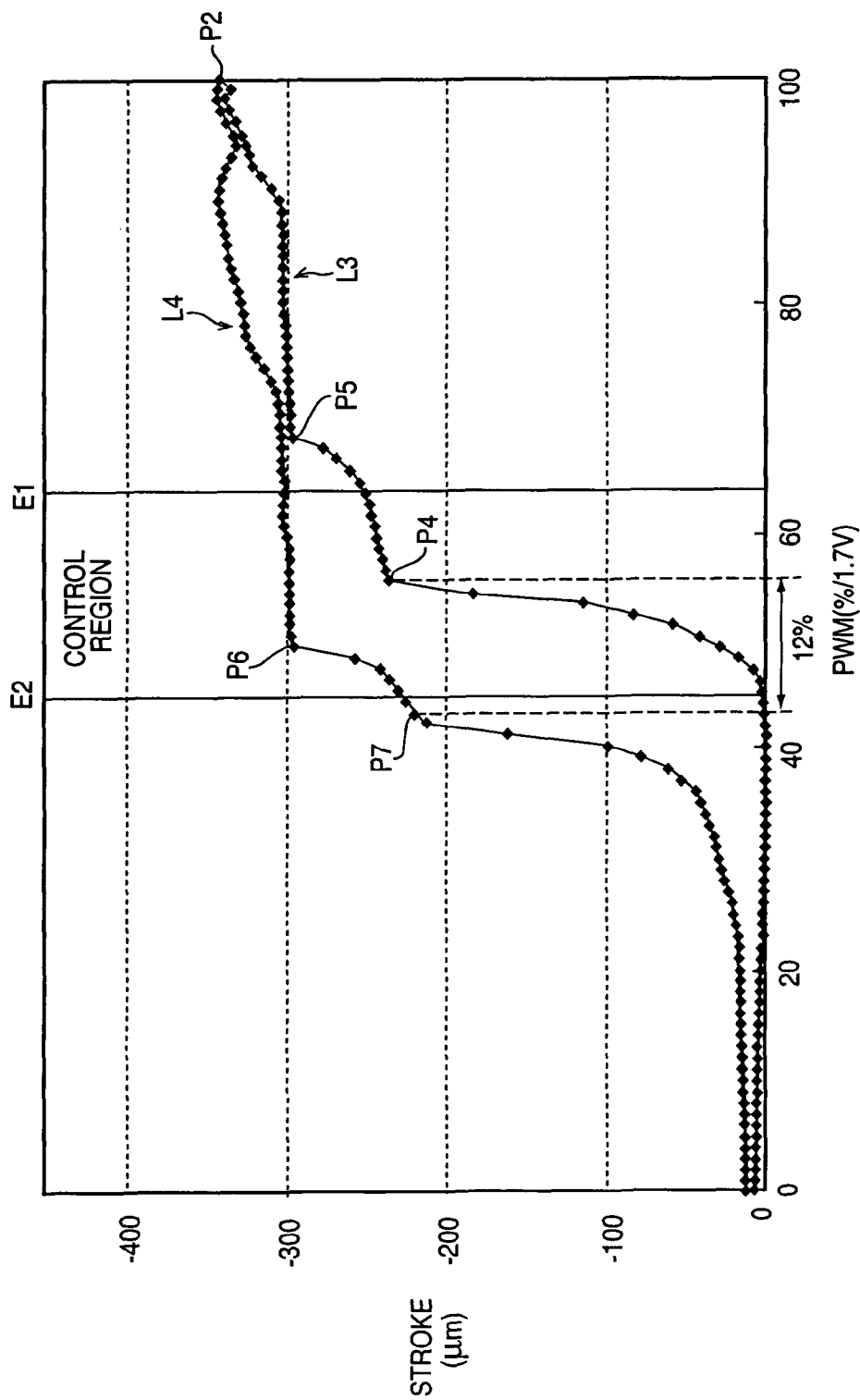
FIG. 21 is a hysteresis property that depicts a relationship between an applied voltage and a switching stroke as pertains to an opening of the electromagnetic valve 38 when the electromagnetic valve 38 is tilted.
Figure 22:
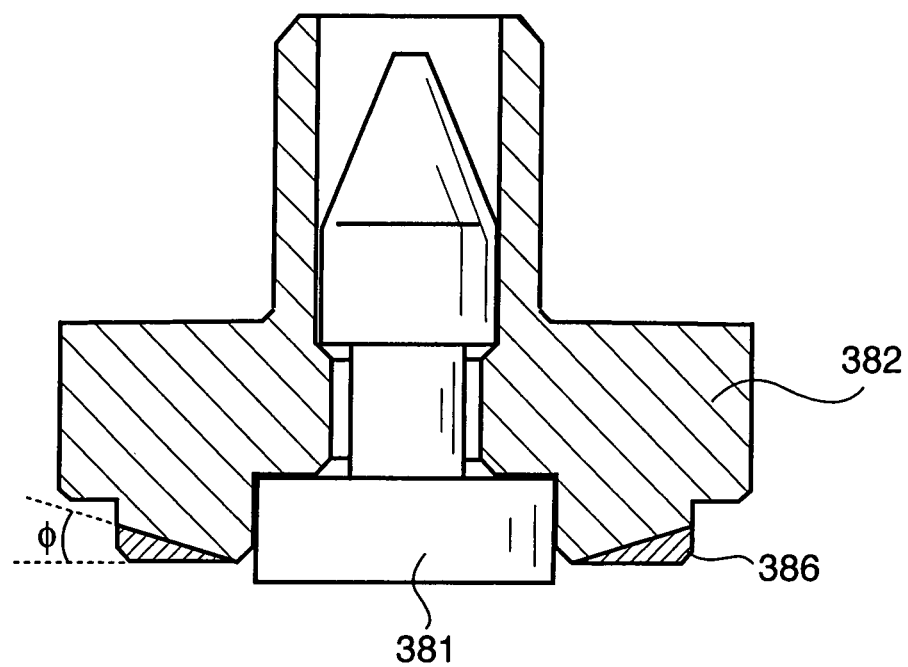
FIG. 22 depicts a suggested modification to an electromagnetic valve.

FIG. 21 depicts a hysteresis property when the electromagnetic valve 38 is closed in such a tilt state.

When a voltage is gradually impressed from the fully open state of the electromagnetic valve 38, as per a curve L3, the electromagnetic valve 38 begins to close at the point when the PWM reaches approximately 40%. When a point P4, i.e., when the PWM approaches approximately 55%, the channel is closed by the rubber valve 381, which is tilted at a slant, as per FIG. 20, i.e., the release stroke approaches approximately −230 μm. Whereas the channel is nearly completely sealed by the deformed elastic rubber valve if further voltage is impressed, the first plunger 382 and the plunger receptacle 383 will make contact at a point P5, which occurs prior to reaching the state of complete seal, i.e., the point P2, and the two will be drawn together by the electromagnetic force arising from the impressed voltage. The first plunger 382 and the plunger receptacle 383 will thus reach the point P2, the state of seal, in the state of being drawn together. In such circumstance, the stroke is approximately −340 μm, similar to FIG. 19.

When releasing the electromagnetic valve 38 from the state of complete seal, i.e., the point P2, as per the curve L4, the impressed voltage is gradually lowered. The deformed rubber valve 381 returns to its original shape according to the fall in impressed voltage, and even in such a state, the first plunger 382 and the plunger receptacle 383 will continue to adhere together because of the electromagnetic force, and the metal contact is released at a point P6, wherein the PWM is approximately 48%, and the release stroke is approximately −300 μm. Even if the voltage enters the control region, there is almost no change in the stroke of the rubber valve 381, before a point P6 is reached, owing to the effect of the adhesion from the electromagnetic force. When the point P6 is passed, the adhesion between the first plunger 382 and the plunger receptacle 383 is broken, and the rubber valve 381 opens dramatically. Consequently, there is a dramatic change in the hysteresis L4. When the point P6 is passed, the electromagnetic valve 38 is in a semi-open state, and air begins to escape through the gap. A further fall in the impressed voltage will completely open the electromagnetic valve 38 at a point P7, wherein the PWM is approximately 43%, and the stroke is approximately −220 μm.

The force that maintains the electromagnetic valve 38 in a closed state between the points P4-P5-P2, and between the points P2-P6, is the electromagnetic force between the first plunger 382 and the plunger receptacle 383 as a result of the impressed voltage, similar to the situation in FIG. 19. Accordingly, the change in stroke between the points P2-P6 is mild. Conversely, after the metal contact is released, i.e., after the point P6, the impressed voltage at the point in time in question, i.e., the PWM, should gradually release the rubber valve 381, thus giving rise to a dramatic stroke change, wherein the rubber valve 381 is completely released at the point P7. When the metal adhesion occurs, the rubber valve 381 begins to open dramatically, i.e., P6, and it becomes difficult to maintain the depressurization speed of approximately 5 mmHg/second. In fact, as depicted in FIG. 21, it is clear that there is no change in the stroke of the rubber valve 381 from the point that the control region is entered until the point P6, and almost no air is escaping.

Whereas the difference in the PWM that opens the rubber valve 381 and the PWM that closes the rubber valve 381 when the electromagnetic valve 38 is operating opening and closing normally, with no metal adhesion occurring, is approximately 6%, the difference in the PWM when metal adhesion has occurred is approximately 12%. The problem is that when such metal adhesion is present, dramatic valve opening and closing operation of the foregoing sort occurs, which interferes with stable exhaust, i.e., depressurization, of the cuff 2. While the problem is solved if the electromagnetic valve 38 can be inserted and removed horizontally at all times, the control thereof is challenging in the extreme.

According to an improvement of the embodiment, a component 386, of the first plunger 382 of the electromagnetic valve 38, that has potential to make contact, is cut so as to taper almost completely in the orientation of the circumference. Making the component 386, that has potential to make contact with the plunger receptacle 383, by tilting the first plunger 382, taper in such fashion, allows maintaining a degree of space between the first plunger 382 and the plunger receptacle 383, thus avoiding metal contact even if the electromagnetic valve 38 should tilt to some extent. Configuring an angle φ of the taper cut component, i.e., No. 386, to be between approximately five degrees and approximately eight degrees, is highly efficacious, as it allows keeping an effect of slanting under control, as well as keeping the electromagnetic force between the first plunger 382 and the plunger receptacle 383 from becoming excessively weak. The angle φ is not limited thereto, however, and tapering to a varying degree will be effective to some extent against slanting.

Tapering the first plunger 382 causes the hysteresis to have the property shown in FIG. 19, even if the rubber valve 381 is slanted, facilitating stable execution of depressurization speed control.

The present invention is not limited to the embodiments described herein. A variety of alterations and transformations are possible without deviating from the spirit or the scope of the present invention. Accordingly, the claims are attached hereinafter in order to publish the scope of the present invention.

CLAIM OF PRIORITY

The present application claims priority based on Japanese Patent Application 2004-264562, filed Sep. 10, 2004, and which is hereby incorporated within in its entirety.

The invention claimed is:

1. A sphygmomanometer, that measures blood pressure in accordance with an oscillation in an artery wall, resulting from an arterial pulse correspondent with a change in cuff pressure, comprising:
 a cuff that is connected to a sphygmomanometer main body by a tube;
 an air supply unit for supplying air to and pressurizing the cuff, the air supply unit being detachable from the sphygmomanometer main body, and forming a single unit when attached to the sphygmomanometer main body;
 a mode switch for selecting a measurement mode from among a Normal mode that measures blood pressure automatically, a Slow mode that measures blood pressure automatically, and a Stethoscope mode for measuring blood pressure manually via a stethoscope;
 a control unit for controlling opening and closing of an electromagnetic valve of the sphygmomanometer to adjust a speed at which air is exhausted from the cuff according to the measurement mode selected via the mode switch so that the control unit controls the electromagnetic valve to: i) keep the exhaust speed at a first preset exhaust speed during blood pressure measurement when the Normal mode is selected by the mode switch; ii) keep the exhaust speed at a second preset exhaust speed during blood pressure measurement when the Slow mode is selected by the mode switch, the second preset exhaust speed being approximately half of the first preset exhaust speed; and iii) keep the exhaust speed at a third preset exhaust speed during blood pressure measurement when the Stethoscope mode is selected by the mode switch, the third preset exhaust speed being approximately the same as the second preset exhaust speed;
 a display unit which displays a blood pressure measurement result and the selected measurement mode,
 a pressure sensor measuring a pressure of the cuff, and
 a memory storing pressure values measured by the pressure sensor during depressurization of the cuff,
wherein
 the control unit determines a systolic blood pressure based on the stored pressure values, identifies a first pressure value from amongst the stored pressure values at which the amplitude dramatically increases for a first time and also identifies a second pressure value from amongst the stored pressure values at which the amplitude dramatically decreases for a first time as seen from a point of maximum amplitude of the pressure,
 the control unit obtains the first pressure value at which the amplitude dramatically increases for a first time as a first systolic blood pressure candidate value,
 the control unit obtains the second pressure value at which the amplitude dramatically decreases for a first time as seen from a point of maximum amplitude of the pressure as a second systolic blood pressure candidate value,
 the control unit determines whether a difference between the first systolic blood pressure candidate value and the second systolic blood pressure candidate value is within a prescribed value, and
 the control unit determines a blood pressure corresponding to the first systolic blood pressure candidate value as the systolic blood pressure when the difference between the first systolic blood pressure candidate value and the second systolic blood pressure candidate value is within a prescribed value.

2. The sphygmomanometer according to claim 1, wherein the cuff is selectable from among a plurality of types of cuffs of different sizes.

3. A sphygmomanometer, that measures blood pressure in accordance with an oscillation in an artery wall, resulting from an arterial pulse correspondent with a change in cuff pressure, comprising:
 a cuff connected to a sphygmomanometer main body by a tube;
 an air supply unit for supplying air to and pressurizing the cuff, the air supply unit being detachable from the sphygmomanometer main body, and forming a single unit when attached to the sphygmomanometer main body;

a mode switch configured to be operated to permit selection, one at a time, of three different measurement modes including a Normal mode during which blood pressure is measured automatically, a Slow mode during which blood pressure is measured automatically, and a Stethoscope mode during which blood pressure is measured manually via a stethoscope;

a control unit configured to control, according to the measurement mode selected by operation of the mode switch, opening and closing of an electromagnetic valve of the sphygmomanometer to adjust a speed at which air is exhausted from the cuff so that: i) whenever the Normal mode is selected through operation of the mode switch the control unit controls the electromagnetic valve to keep the exhaust speed at a first preset exhaust speed during blood pressure measurement; ii) whenever the Slow mode is selected through operation of the mode switch the control unit keeps the exhaust speed at a second preset exhaust speed during blood pressure measurement, wherein the second preset exhaust speed is approximately half of the first preset exhaust speed; and iii) whenever the Stethoscope mode is selected through operation of the mode switch the control unit keeps the exhaust speed at a third preset exhaust speed during blood pressure measurement, wherein the third preset exhaust speed is approximately the same as the second preset exhaust speed;

a display unit which displays a blood pressure measurement result and the selected measurement mode, a pressure sensor measuring a pressure of the cuff, and a memory containing stored pressure values measured by the pressure sensor during depressurization of the cuff, wherein the control unit determines a systolic blood pressure based on the stored pressure values, identifies a first pressure value from amongst the stored pressure values at which the amplitude dramatically increases for a first time and also identifies a second pressure value from amongst the stored pressure values at which the amplitude dramatically decreases for a first time as seen from a point of maximum amplitude of the pressure, the control unit obtains the first pressure value at which the amplitude dramatically increases for a first time as a first systolic blood pressure candidate value, the control unit obtains the second pressure value at which the amplitude dramatically decreases for a first time as seen from a point of maximum amplitude of the pressure as a second systolic blood pressure candidate value, the control unit determines whether a difference between the first systolic blood pressure candidate value and the second systolic blood pressure candidate value is within a prescribed value, and the control unit determines a blood pressure corresponding to the first systolic blood pressure candidate value as the systolic blood pressure when the difference between the first systolic blood pressure candidate value and the second systolic blood pressure candidate value is within a prescribed value.

4. The sphygmomanometer according to claim 3, wherein the cuff is selectable from among a plurality of types of cuffs of different sizes.

* * * * *